United States Patent
Samaniego et al.

(10) Patent No.: US 10,842,910 B2
(45) Date of Patent: Nov. 24, 2020

(54) SYSTEMS FOR DRYING SHEETS OF DONOR-PROVIDED HUMAN TISSUE

(71) Applicant: AlloSource, Centennial, CO (US)

(72) Inventors: Adrian C. Samaniego, Highlands Ranch, CO (US); Matthew Southard, Denver, CO (US)

( * ) Notice: Subject to any disclaimer, the term of this patent is extended or adjusted under 35 U.S.C. 154(b) by 260 days.

(21) Appl. No.: 15/707,796

(22) Filed: Sep. 18, 2017

(65) Prior Publication Data

US 2018/0000986 A1  Jan. 4, 2018

Related U.S. Application Data

(62) Division of application No. 14/562,353, filed on May 12, 2014, now Pat. No. 9,795,707.

(60) Provisional application No. 61/913,034, filed on Dec. 6, 2013.

(51) Int. Cl.
  *A61L 26/00* (2006.01)
  *A61L 27/36* (2006.01)

(52) U.S. Cl.
  CPC ......... *A61L 26/0061* (2013.01); *A61L 27/362* (2013.01); *Y10T 156/10* (2015.01)

(58) Field of Classification Search
  CPC ... A61L 26/0061; A61L 27/362; Y10T 156/10
  USPC ....................................... 422/536
  See application file for complete search history.

(56) References Cited

U.S. PATENT DOCUMENTS

| | | | |
|---|---|---|---|
| 4,361,552 A | | 11/1982 | Baur |
| 4,801,553 A | * | 1/1989 | Owen .................. G01N 1/36 118/429 |
| 5,217,627 A | * | 6/1993 | Pall .................... A61J 1/05 210/257.1 |
| 5,336,616 A | | 8/1994 | Livesey et al. |
| 5,723,010 A | | 3/1998 | Yui et al. |
| 5,782,914 A | * | 7/1998 | Schankereli ........ A61L 27/3604 435/1.1 |
| 5,837,278 A | | 11/1998 | Geistlich et al. |
| 5,843,766 A | * | 12/1998 | Applegate ............. C12M 21/08 435/284.1 |

(Continued)

FOREIGN PATENT DOCUMENTS

| | | |
|---|---|---|
| CN | 101889569 | 5/2013 |
| WO | 2009132186 A1 | 10/2009 |

(Continued)

*Primary Examiner* — Benjamin R Whatley
*Assistant Examiner* — Jacqueline Brazin
(74) *Attorney, Agent, or Firm* — Kilpatrick Townsend & Stockton LLP

(57) ABSTRACT

Embodiments of this technology may include an apparatus for drying tissue. The apparatus may include human donor tissue placed in contact with and between at least two layers of backing material. This tissue and backing layer may then be restrained by two plates. This tissue may be amniotic tissue. The backing layer may include woven or nonwoven material. This backing layer may be wetted with a saline solution. At least one of the plates of the tissue drying apparatus may be perforated. The tissue assembly along with the plates may then be placed inside a chamber configured to receive the plates and tissue assembly. The chamber may be configured so that gas can be forced into the chamber with the gas flow going around the plates and the tissue assembly.

18 Claims, 25 Drawing Sheets

(56) References Cited

U.S. PATENT DOCUMENTS

| | | | |
|---|---|---|---|
| 5,876,451 A | 3/1999 | Yui et al. | |
| 5,989,498 A | 11/1999 | Odland | |
| 6,152,142 A | 11/2000 | Tseng | |
| 6,326,019 B1 | 12/2001 | Tseng | |
| 6,432,710 B1 | 8/2002 | Boss | |
| 6,562,616 B1* | 5/2003 | Toner | C12M 29/10 435/293.1 |
| 7,159,510 B2 | 1/2007 | Lamaster et al. | |
| 7,347,876 B2 | 3/2008 | Tsai | |
| 7,393,437 B2 | 7/2008 | Chan | |
| 7,494,802 B2 | 2/2009 | Tseng | |
| 7,723,108 B2 | 5/2010 | Truncale et al. | |
| 7,727,550 B2 | 6/2010 | Siegal et al. | |
| 7,824,671 B2 | 11/2010 | Binder | |
| 7,902,145 B2 | 3/2011 | Chu | |
| 8,021,692 B2 | 9/2011 | Hiles | |
| 8,058,066 B2 | 11/2011 | Marshall | |
| 8,071,135 B2 | 12/2011 | Liu et al. | |
| 8,105,634 B2 | 1/2012 | Liu et al. | |
| 8,153,162 B2 | 4/2012 | Tseng | |
| 8,158,141 B2 | 4/2012 | Chen | |
| 8,182,840 B2 | 5/2012 | Tseng | |
| 8,182,841 B2 | 5/2012 | Tseng | |
| 8,187,639 B2 | 5/2012 | Tseng | |
| 8,198,245 B2 | 6/2012 | Niklason | |
| 8,231,908 B2 | 7/2012 | Kinoshita | |
| 8,323,701 B2 | 12/2012 | Daniel et al. | |
| 8,357,403 B2 | 1/2013 | Daniel et al. | |
| 8,372,437 B2 | 2/2013 | Daniel | |
| 8,372,438 B2 | 2/2013 | Daniel et al. | |
| 8,372,439 B2 | 2/2013 | Daniel et al. | |
| 8,409,626 B2 | 4/2013 | Daniel | |
| 8,420,126 B2 | 4/2013 | Tseng | |
| 8,440,235 B2 | 5/2013 | Tseng | |
| 8,455,009 B2 | 6/2013 | Tseng et al. | |
| 8,460,714 B2 | 6/2013 | Tseng et al. | |
| 8,597,687 B2 | 12/2013 | Daniel et al. | |
| 8,642,092 B2 | 2/2014 | Daniel et al. | |
| 8,703,206 B2 | 4/2014 | Daniel et al. | |
| 8,703,207 B2 | 4/2014 | Daniel et al. | |
| 8,709,493 B2 | 4/2014 | Daniel et al. | |
| 8,709,494 B2 | 4/2014 | Daniel | |
| 8,822,415 B2 | 9/2014 | Trumpower et al. | |
| 8,840,665 B2 | 9/2014 | Young et al. | |
| 8,883,210 B1 | 11/2014 | Truncale et al. | |
| 9,084,767 B2 | 7/2015 | Daniel et al. | |
| 9,186,382 B2 | 11/2015 | Daniel et al. | |
| 9,265,800 B2 | 2/2016 | Daniel | |
| 9,265,801 B2 | 2/2016 | Daniel | |
| 9,272,003 B2 | 3/2016 | Daniel et al. | |
| 9,272,005 B2 | 3/2016 | Daniel | |
| 9,795,707 B2 | 10/2017 | Samaniego et al. | |
| 2003/0187515 A1 | 10/2003 | Hariri et al. | |
| 2003/0212454 A1* | 11/2003 | Scott | A61F 2/2412 623/2.14 |
| 2004/0048796 A1 | 3/2004 | Hariri | |
| 2004/0134088 A1 | 7/2004 | Meyer | |
| 2005/0019865 A1 | 1/2005 | Kihm | |
| 2005/0058631 A1 | 3/2005 | Kihm | |
| 2006/0234376 A1 | 10/2006 | Mistry | |
| 2007/0160588 A1 | 7/2007 | Kihm | |
| 2008/0046095 A1 | 2/2008 | Daniel | |
| 2008/0069895 A1 | 3/2008 | Liu et al. | |
| 2008/0249276 A1* | 10/2008 | Alder | B32B 27/00 528/10 |
| 2009/0258082 A1 | 10/2009 | Nikaido et al. | |
| 2010/0112543 A1 | 5/2010 | Ngo | |
| 2010/0196478 A1 | 8/2010 | Masters | |
| 2010/0304487 A1 | 12/2010 | Truncale | |
| 2011/0091434 A1 | 4/2011 | Miller | |
| 2011/0104100 A1 | 5/2011 | Riordan | |
| 2011/0129520 A1 | 6/2011 | Bogdansky et al. | |
| 2011/0160857 A1 | 6/2011 | Bracone | |
| 2011/0177150 A1 | 7/2011 | Pathak et al. | |
| 2011/0206776 A1 | 8/2011 | Tom et al. | |
| 2011/0256202 A1 | 10/2011 | Tom et al. | |
| 2011/0262393 A1 | 10/2011 | Yang | |
| 2012/0009644 A1 | 1/2012 | Hanby et al. | |
| 2012/0009679 A1 | 1/2012 | Hanby et al. | |
| 2012/0010725 A1 | 1/2012 | Hanby et al. | |
| 2012/0063997 A1 | 3/2012 | Hunter | |
| 2012/0078378 A1 | 3/2012 | Daniel et al. | |
| 2012/0083900 A1 | 4/2012 | Samaniego et al. | |
| 2012/0141595 A1 | 6/2012 | Tseng et al. | |
| 2012/0142102 A1 | 6/2012 | Chen | |
| 2012/0164114 A1 | 6/2012 | Abbot | |
| 2012/0189583 A1 | 7/2012 | Liu et al. | |
| 2012/0189586 A1 | 7/2012 | Harrell | |
| 2012/0191184 A1 | 7/2012 | Chen | |
| 2012/0201787 A1 | 8/2012 | Abbot | |
| 2012/0225484 A1 | 9/2012 | Bhatia et al. | |
| 2012/0269774 A1 | 10/2012 | Ichim | |
| 2012/0276080 A1 | 11/2012 | Kinoshita et al. | |
| 2012/0294810 A1 | 11/2012 | Daniel | |
| 2012/0294811 A1 | 11/2012 | Daniel | |
| 2012/0294908 A1 | 11/2012 | Daniel et al. | |
| 2012/0294910 A1 | 11/2012 | Daniel et al. | |
| 2012/0328690 A1 | 12/2012 | Tseng et al. | |
| 2013/0004465 A1 | 1/2013 | Aberman | |
| 2013/0006385 A1 | 1/2013 | Daniel | |
| 2013/0052169 A1 | 2/2013 | Marom | |
| 2013/0158658 A1 | 6/2013 | Hayzlett | |
| 2013/0202676 A1 | 8/2013 | Koob et al. | |
| 2013/0204393 A1 | 8/2013 | Samaniego | |
| 2013/0211511 A1 | 8/2013 | Young | |
| 2013/0218274 A1 | 8/2013 | Spencer et al. | |
| 2013/0230561 A1 | 9/2013 | Daniel et al. | |
| 2013/0247517 A1 | 9/2013 | Samaniego et al. | |
| 2013/0344162 A1 | 12/2013 | Morse et al. | |
| 2014/0017280 A1 | 1/2014 | Daniel et al. | |
| 2014/0037598 A1 | 2/2014 | Jansen et al. | |
| 2014/0050788 A1 | 2/2014 | Daniel et al. | |
| 2014/0052247 A1 | 2/2014 | Daniel et al. | |
| 2014/0052274 A1 | 2/2014 | Koob et al. | |
| 2014/0106447 A1 | 4/2014 | Brown et al. | |
| 2014/0127177 A1 | 5/2014 | Tom et al. | |
| 2014/0127317 A1 | 5/2014 | Jansen et al. | |
| 2014/0140964 A1 | 5/2014 | Brown et al. | |
| 2014/0140966 A1 | 5/2014 | Tom et al. | |
| 2014/0205646 A1 | 7/2014 | Morse et al. | |
| 2014/0214176 A1 | 7/2014 | Daniel et al. | |
| 2014/0234387 A1 | 8/2014 | Daniel et al. | |
| 2014/0255496 A1 | 9/2014 | Daniel et al. | |
| 2014/0255508 A1 | 9/2014 | Morse et al. | |
| 2014/0277579 A1 | 9/2014 | Young et al. | |
| 2014/0294777 A1 | 10/2014 | Tom et al. | |
| 2014/0301986 A1 | 10/2014 | Tom et al. | |
| 2014/0302162 A1 | 10/2014 | Morse et al. | |
| 2014/0343688 A1 | 11/2014 | Morse et al. | |
| 2014/0348940 A1 | 11/2014 | Murphy et al. | |
| 2015/0010506 A1 | 1/2015 | Jansen et al. | |
| 2015/0010609 A1 | 1/2015 | Tom et al. | |
| 2015/0010610 A1 | 1/2015 | Tom et al. | |
| 2015/0091219 A1* | 4/2015 | Munnelly | A61F 2/2412 264/479 |
| 2015/0140114 A1 | 5/2015 | Sasko | |
| 2015/0174297 A1 | 6/2015 | Daniel | |
| 2015/0209475 A1 | 6/2015 | Daniel | |
| 2015/0265747 A1 | 9/2015 | Daniel | |
| 2016/0129154 A1 | 5/2016 | Hopkinson et al. | |
| 2016/0136334 A1 | 5/2016 | Schorgl et al. | |

FOREIGN PATENT DOCUMENTS

| | | |
|---|---|---|
| WO | 2012083021 A1 | 6/2012 |
| WO | 2012083023 A1 | 6/2012 |
| WO | 2012088396 A2 | 6/2012 |
| WO | 2012112410 | 8/2012 |
| WO | 2012112417 | 8/2012 |
| WO | 2012112441 | 8/2012 |
| WO | 2012116372 A1 | 8/2012 |
| WO | 2012136701 A1 | 10/2012 |

(56) References Cited

FOREIGN PATENT DOCUMENTS

| WO | 2012170905 A1 | 12/2012 |
| WO | 2013032938 A1 | 3/2013 |

* cited by examiner

SYSTEMS FOR DRYING SHEETS OF DONOR-PROVIDED HUMAN TISSUE

CROSS-REFERENCES TO RELATED APPLICATIONS

This application is a divisional of U.S. application Ser. No. 14/562,353, filed Dec. 5, 2014, which claims the benefit of priority to U.S. Provisional Application No. 61/913,034, filed Dec. 6, 2013. U.S. Provisional Application No. 61/913,034 is related to U.S. Pat. Nos. 9,358,320, 9,480,549, and 9,616,152. The entire contents of the above filings are incorporated herein by reference.

BACKGROUND

Embodiments of the present invention are directed in general to the field of medical dressings, and in particular to methods and apparatus for drying tissue compositions.

Many types of human tissue can be used to help treat a variety of ailments, including for wound care and burn care. One type of human tissue is birth tissue. Human birth tissue can be defined as the amniotic sac (which includes two tissue layers, the amnion and chorion), the placenta, the umbilical cord, and the cells of fluid contained in each. Human amniotic membrane has been used for many years in various surgical procedures, including skin transplantation and ocular surface disorder treatments to prevent adhesions. Lately, certain known medical techniques involve the application of amnion tissue to patients in the form of surgical dressings. Although amniotic compositions and methods are presently available and provide real benefits to patients in need thereof, many advances may still be made providing improved dressing systems and manufacturing methods. The dressing systems and manufacturing methods described herein provide further solutions and answers to these outstanding needs.

BRIEF SUMMARY

Tissue dressings, such as amniotic tissue dressings, can be used to treat patients. Such dressings can be used to treat patients having tarsal tunnel syndrome, iliotibial band stenosis, phantom pain associated with amputation, damaged meniscus, peripheral nerve damage or injuries, and the like. Further, dressings can be used in spinal treatments including laminectomies, anterior lumbar interbody fusion (ALIF) procedures, laminotomies, and in extensor halgus longus tendon surgeries. These tissue dressings may be more easily applied and may more easily adhere as dry tissue, relatively salt free tissues, tissues that are flat sheets with minimal wrinkles, or supple and pliable tissues. Embodiments of the technology described herein encompass techniques for drying the tissue, removing salt crystals, while preserving other properties of the tissue without prohibitively significant investments in capital or time. These drying methods may avoid a chalky, white, inconsistent appearance in the tissue. In addition, the drying methods may prevent the tissue from turning a dark brown color. The drying methods also may avoid excessive wrinkling and size deformation in the tissue. With these methods, the tissues may not become more brittle. Rather, the tissues may have properties similar to cling wrap, allowing the tissue to stick easily to the surface to be treated.

In one aspect, embodiments of the technology may involve a method of processing the human donor tissue for administration to a recipient. This method may include the step of contacting the human donor tissue with a backing layer, where the human donor tissue and the backing layer contain a saline solution. This saline solution may include a solvent and a disassociated salt. The method may further include evaporating a portion of the solvent from a surface of the backing layer to form a dry tissue. The evaporation of the solvent may move a portion of the disassociated salt from the human donor tissue to the backing layer. This process may then result in a tissue that is mostly dry and free of salt crystals.

The tissue may be amniotic tissue. This tissue may be treated with glutaraldehyde and then rinsed with a saline solution. The saline solution may be the same or different as the saline solution contained in the backing layer. The solvent in the solution may be water. The tissue itself may be a single layer or multiple layers of tissues. The backing material may be in the form of sheets. The backing layer may also be of woven or nonwoven material. The tissue assembly, comprising the tissue and backing layer, may be pressed together to provide better contact between the backing layer and the tissue and to reduce air pockets and excess moisture.

The backing layer may be in contact with a plate. The human donor tissue may be restrained between the first plate and a second plate. The plates used in the tissue assembly may be perforated. The plates may be perforated to the extent such that 5-95% of the plate area is open. These plates may be clamped around the tissue assembly to help the tissue remain flat, with little or no wrinkling.

Evaporating the solvent may be accomplished using forced gas flow. The drying of the tissue assembly may be done in a chamber. The chamber may or may not include heating. The heating may be done by heating the chamber itself or by heating the forced gas before it reaches the chamber. The heating may include temperatures of below about 40° C., temperatures of below about 25° C., temperatures between about 5 and about 15° C., or no heating at all. The drying may be done with a forced gas flow for at least 1.5 hours. The drying process may also include moving the plates mechanically, possibly like a windmill or fan. The plates may be moved for all, substantially all, or a portion of the drying process, and moving the plates may not include transferring the plates into or out of the chamber. The movement may reduce the amount of forced gas flow needed, the heating temperature, or the drying time.

The final tissue produced may be a flat sheet with minimal wrinkles. The tissue may have a moisture content of less than 10% or it may be less than 5%. The dry tissue may reach an equilibrium moisture content, where the tissue will not absorb a significant quantity of moisture when exposed to the ambient atmosphere for an extended period of time.

After the drying process, the tissue may be rehydrated. The backing layer may also be removed from the tissue. The tissue also may be trimmed to remove some areas with discoloration or other undesired property.

In another aspect, embodiments of this technology may include a method of processing an amniotic tissue for administration to a recipient patient. The method may include treating the amniotic tissue with a glutaraldehyde solution. Additionally, the method may include rinsing the amniotic tissue with a first saline solution. The method may further include contacting the amniotic tissue with a first backing layer and a second backing layer. The amniotic tissue may contain a second saline solution that includes a solvent and a dissociated salt. The first and second backing layers may contain the second saline solution.

The method may include restraining the amniotic tissue, the first backing layer, and the second backing layer between a first plate and a second plate. The method may also include pressing together the amniotic tissue and the first and second backing layers. The method may further include evaporating a portion of the solvent from a surface of the first or the second backing layer, which may move a portion of the dissociated salt from the amniotic tissue into the first or second backing layer. Evaporating may include maintaining a temperature around the amniotic tissue below about 40° C.

In another aspect, embodiments of this technology may also include an apparatus for drying tissue. The apparatus may include human donor tissue placed in contact with and between at least two layers of backing material. This tissue and backing layer may then be restrained by two plates. This tissue may be amniotic tissue. The backing layer may include woven or nonwoven material. This backing layer may be wetted with a saline solution.

At least one of the plates of the tissue drying apparatus may be perforated. The tissue assembly along with the plates may then be placed inside a chamber configured to receive the plates and tissue assembly. The chamber may be configured so that gas can be forced into the chamber with the gas flow going around the plates and the tissue assembly.

In another aspect, embodiments of this technology may also include a dry, mostly salt crystal free, pliable tissue with minimal wrinkles, produced by the various embodiments of this invention. This tissue may be amniotic tissue.

DETAILED DESCRIPTION

Embodiments of the present invention encompass systems and methods for processing tissue for use in wound care, so as to allow removal of water and salt crystals without creating significant wrinkling or discoloration. In addition such drying methods may allow for amnion tissue to have desirable properties such as pliability, suppleness, and clinginess when rehydrated. These dried tissues may easily be applied to and adhere to wounds or other treatment areas.

Figure 1:
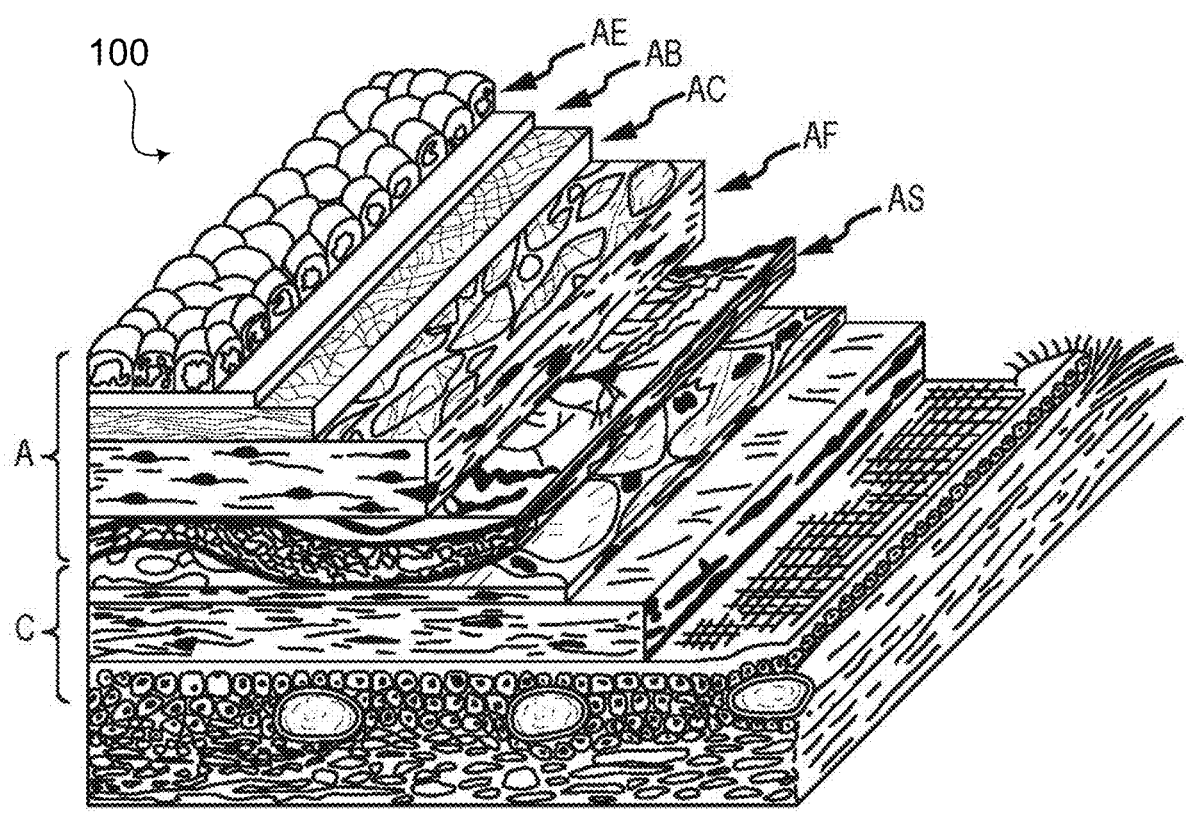
FIG. 1 shows a cross-sectional view of the tissue structure of a segment of the fetal sac, according to embodiments of the present invention.

Turning to the drawings, FIG. 1 illustrates tissue features of a human fetal sac structure 100, including the anatomy of the amnion A and chorion C. As shown here, the amnion layer has several cell layers and has two sides with different cellular components. According to this depiction, the amnion A includes a single layer of ectodermally derived columnar epithelial cells AE adhered to a basement membrane AB. In turn the basement membralle AB includes collagen I, collagen III, collagen IV, laminin, glycosaminoglycans, and fibronectin, and is attached to an underlying layer of connective tissue. The connective tissue includes an acellular compact layer AC of reticular fibers, a fibroblast layer AF, and a spongy layer AS (referred to as Wharton's jelly) which form a network of fine fibrils surrounded by mucus. When the amnion A is separated from the chorion C, a two sided, asymmetrical tissue is produced having an epithelial layer AE with epithelial cells on one side and a fibroblast layer AF on the opposite side. Hence, the separated amnion A includes an epithelial layer AE on one side and a fibroblast layer AF on the opposing side. Between the epithelial and fibroblast layers is a basement membrane AB and a compact layer AC. The fibroblast layer may be considered to include a loose network of reticulum containing fibroblasts. The fibroblast layer also typically includes collagen (e.g. Types I, III, and VI) and glycoproteins (e.g. nidogen, laminin, and fibronectin).

Figure 2:
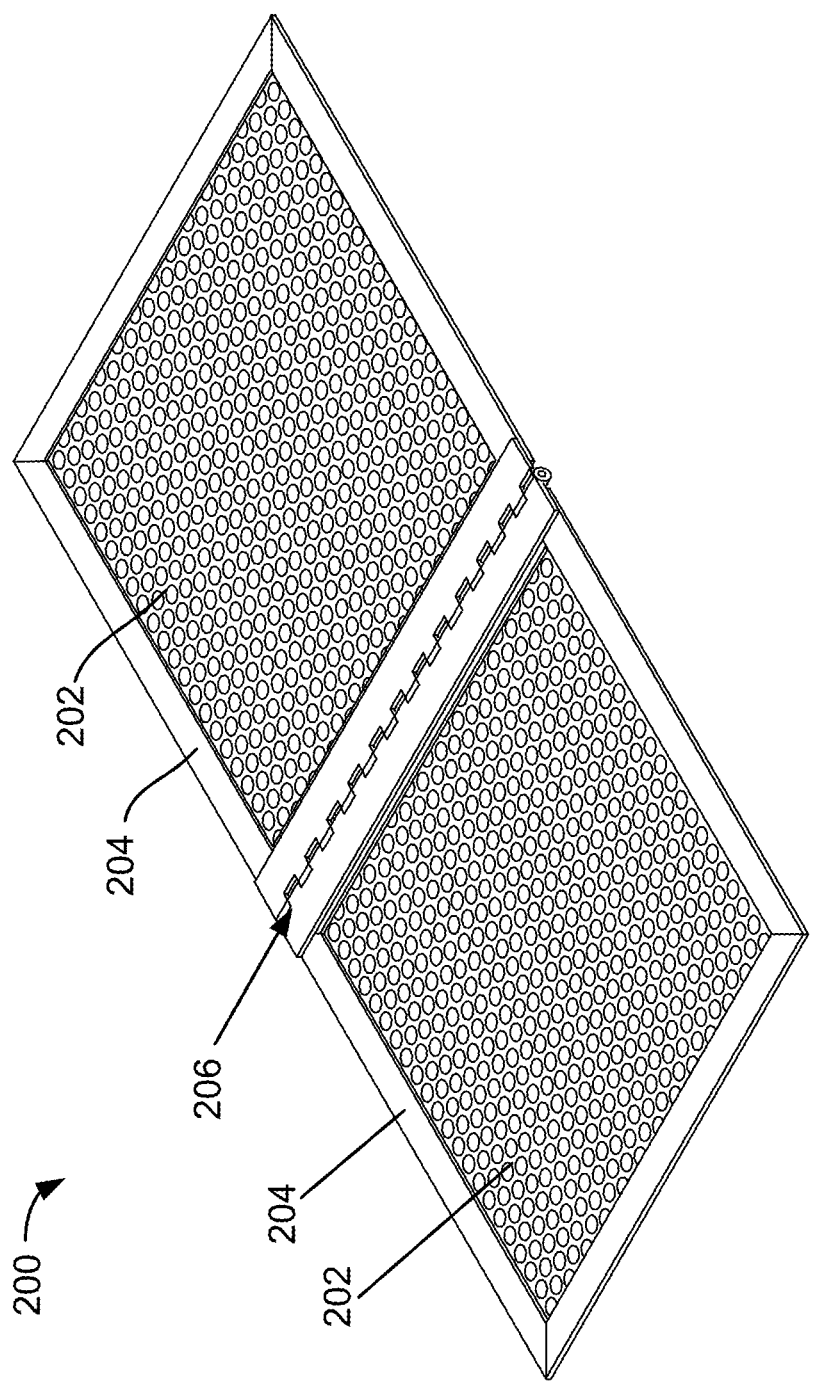
FIG. 2 shows aspects of the plate assembly used to sandwich the tissue, according to embodiments of the present invention.

FIG. 2 shows an embodiment of the plate assembly 200 used in sandwiching the tissue assembly. These plates may be made out of stainless steel, aluminum, or some other material. These plates may be perforated, with over 50% of the surface area open. In some embodiments, over 70% of the surface area may be open. The perforated holes may be hexagonal, circular, elliptical, or some other shape. The drawing shows the main plates 202 surrounded by supports 204. The two plates and supports are connected by hinges 206. The hinges allow the plates to close around the tissue assembly. When closed, the plates may be parallel to each other.

Figure 3:
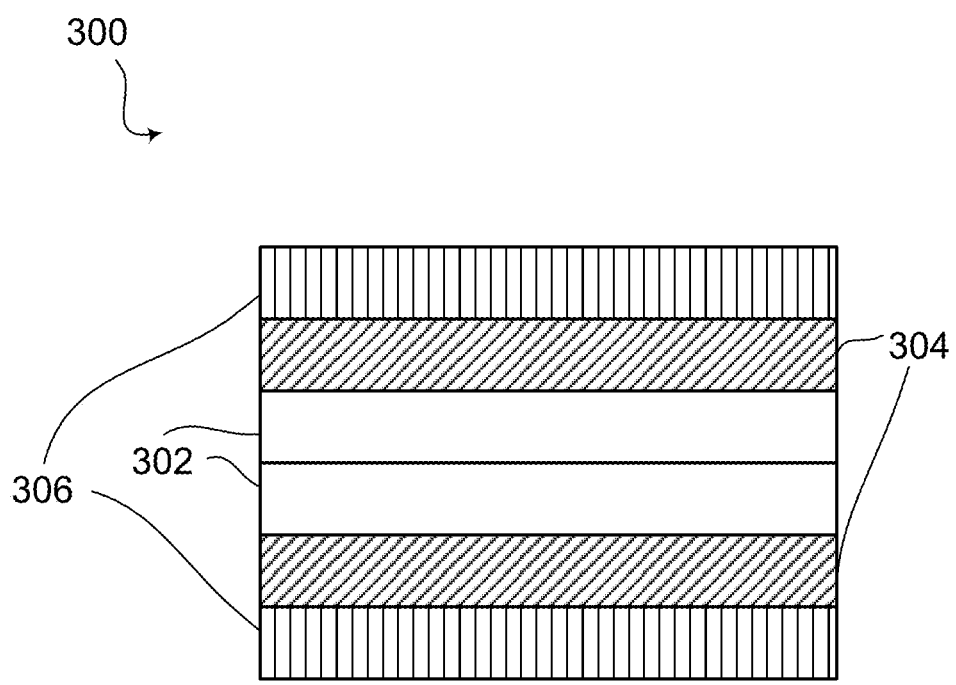
FIG. 3 illustrates the pressed tissue assembly, according to embodiments of the present invention.

FIG. 3 shows an embodiment of the pressed tissue assembly sandwich 300. The amniotic tissues 302 are sandwiched between the backing layers 304. This sandwich is further surrounded by the plates 306. The plates 306 may be the same plates 202 in FIG. 2. As discussed below, the sandwich may be placed into a chamber for drying so as to remove solvent from the tissue and backing layer material.

Figure 4A:
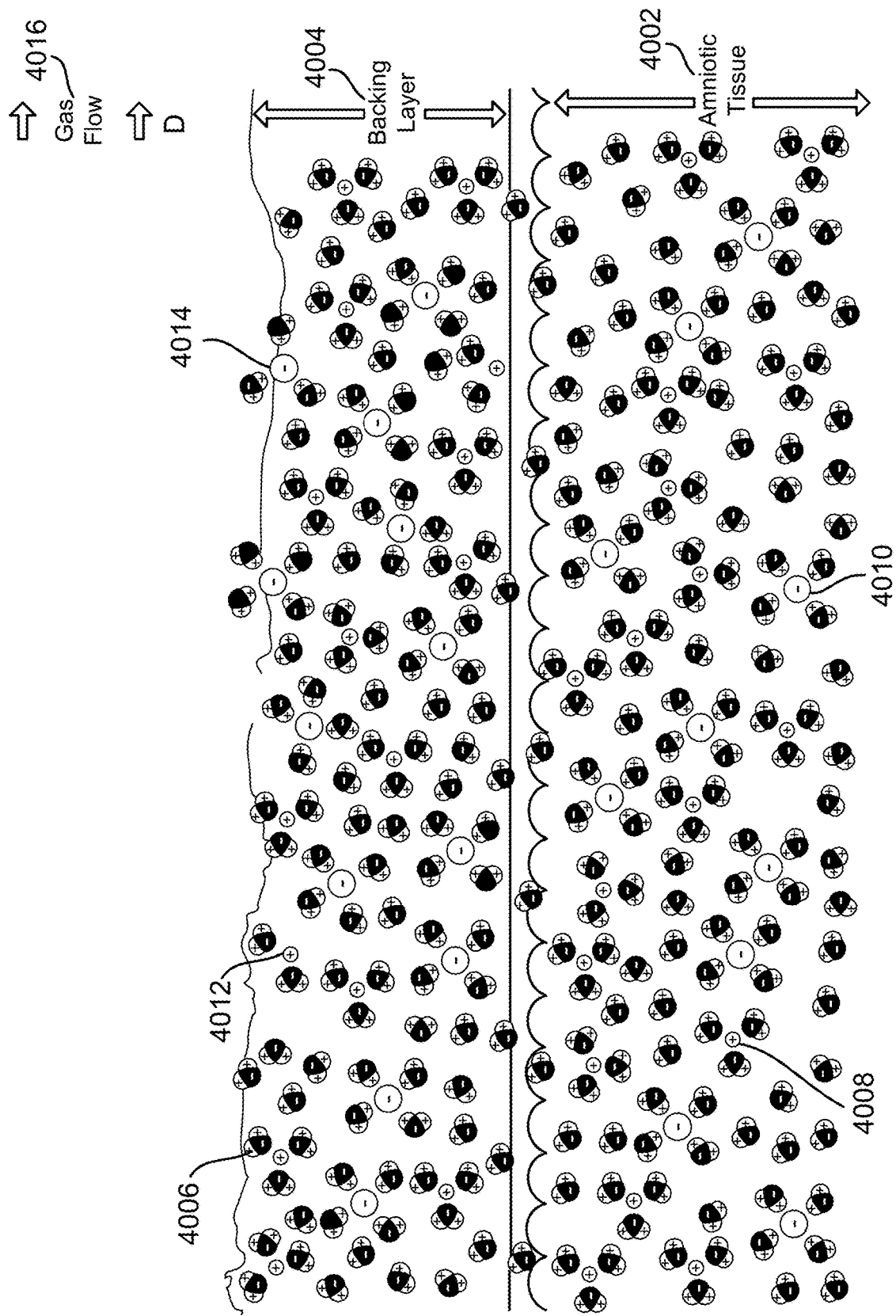
FIGS. 4A, 4B, 4C, 4D, 4E, 4F, 4G, 4H, 4I, 4J, 4K, and 4L show the conceptualized movement of water and salt from the tissue to the backing layer and into the gas, according to embodiments of the present invention.

FIG. 4A shows the solvent and salt concentration in the amniotic tissue 4002 and backing layer 4004 at time equal to $t_0$, the beginning of the drying process. The solvent in the figure is water. Water molecules, such as 4006, are present in both the amniotic tissue 4002 and backing layer 4004. The salt exists in dissociated form (cation 4008 and anion 4010) in the amniotic tissue 4002, and the salt is in dissociated form (cation 4012 and anion 4014) in the backing layer 4004. At time $t_0$, gas flow 4016 has just begun. The gas flows in a direction, as depicted by arrow D.

Figure 4B:
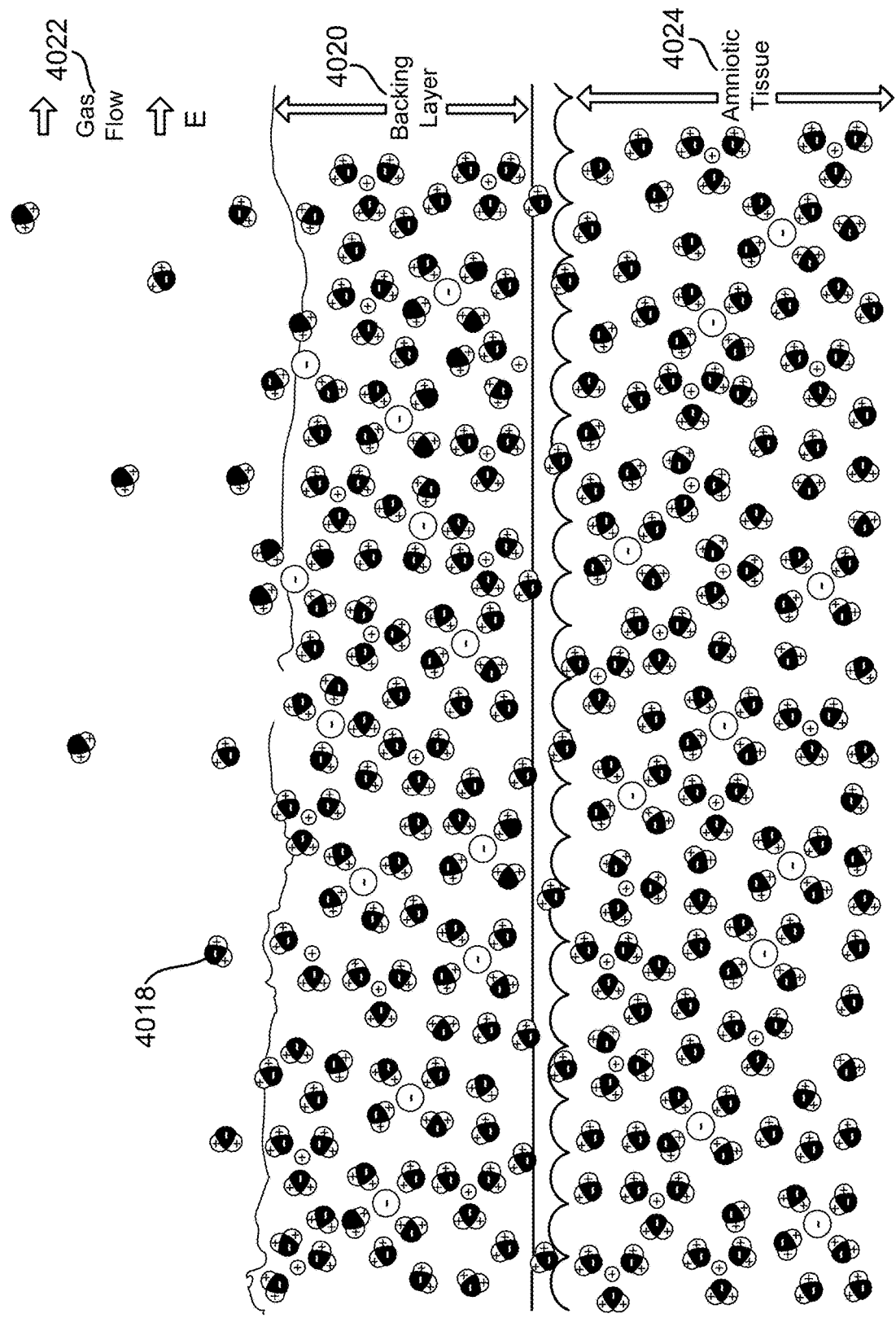

FIG. 4B depicts the drying process at a time equal to $t_1$, where $t_1$ is greater than $t_0$. Water 4018 leaves the backing layer 4020 with the gas flow 4022 in the direction of arrow E. At this point, the salt ion concentrations in the amniotic tissue 4024 and backing layer 4020 are about the same as at time $t_0$, in FIG. 4A.

Figure 4C:
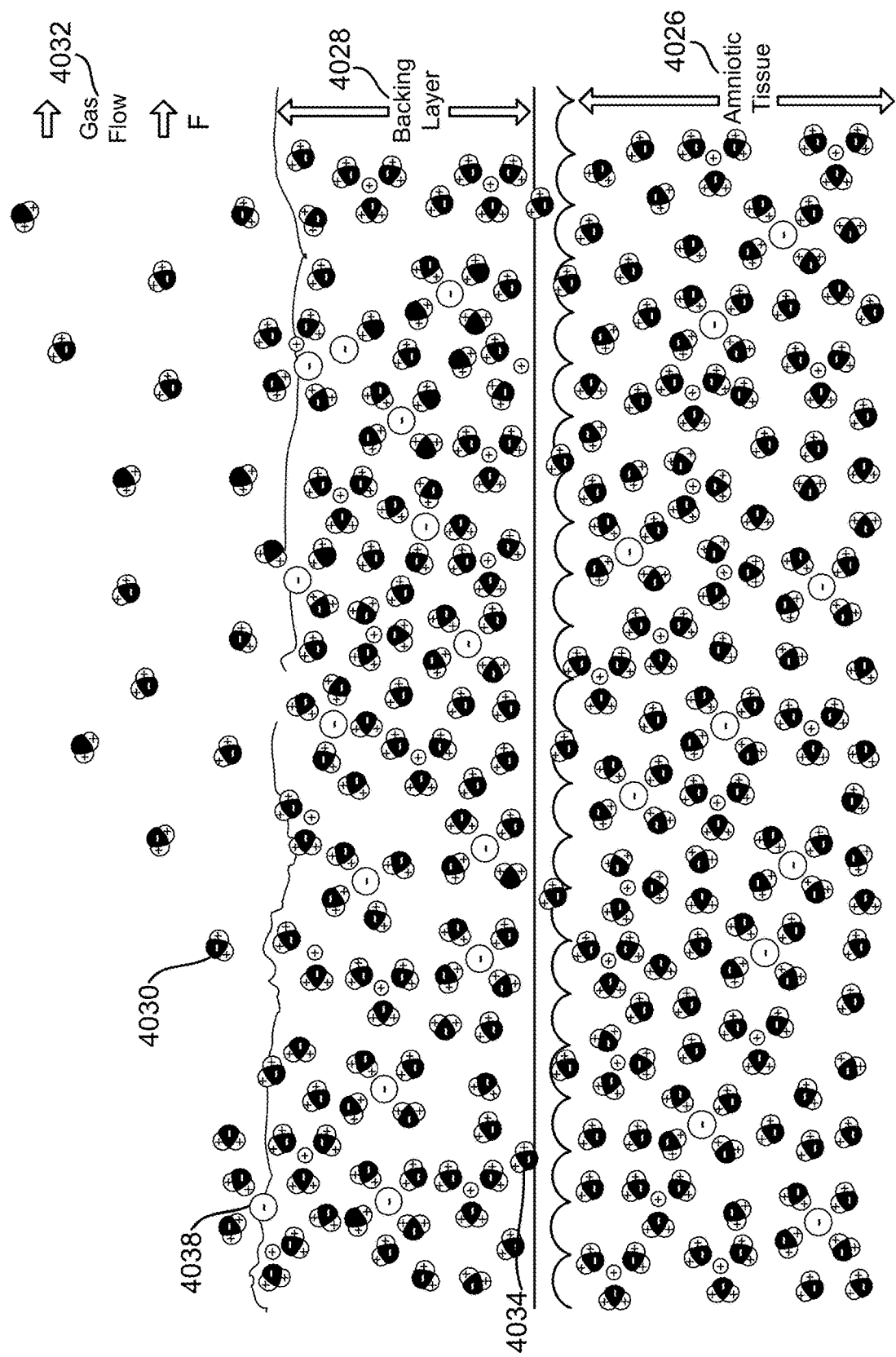

FIG. 4C shows continued drying of the tissue 4026 and backing layer 4028 at time equal to $t_2$, where $t_2$ is greater than $t_1$. Following a period of drying, more water molecules 4030 go into the gas flow 4032, which moves in the direction as indicated by arrow F. In addition, fewer water molecules 4034 are present at the surface of the backing layer 4036 closest to the amniotic tissue 4026 than at time equal to $t_1$ in FIG. 4B. Salt ions 4038 in the backing layer 4028 move along with the water toward the gas flow 4032.

Figure 4D:
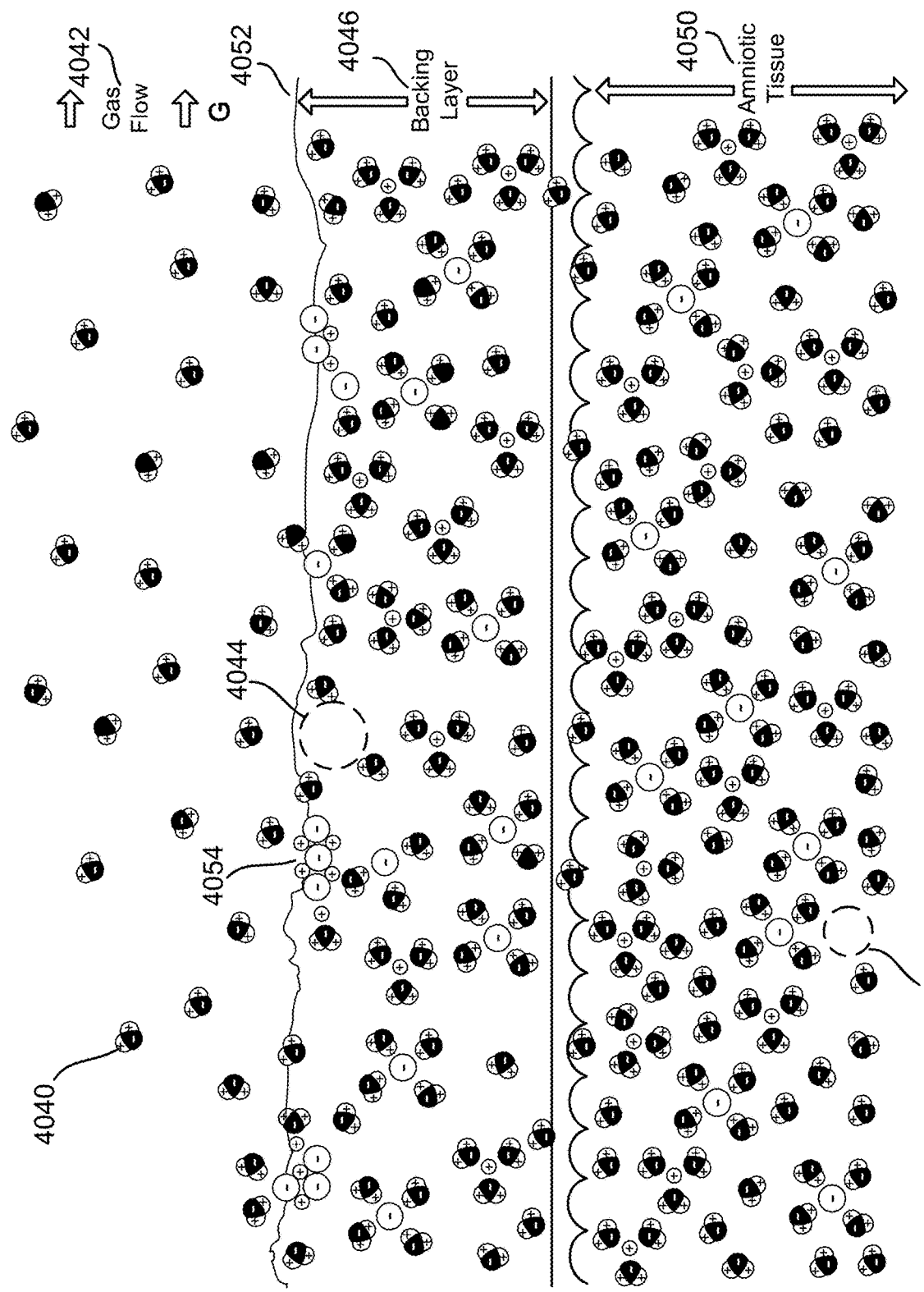

In FIG. 4D, the drying process continues at time equal to $t_3$, where $t_3$ is greater than $t_2$. More water 4040 continues to escape to the gas flow 4042, moving in a direction indicated by arrow G. This leaves areas 4044 of no water in the backing layer 4046 and areas 4048 of no water in the amniotic tissue 4050. As more water leaves the backing layer, the salt ions near the surface 4052 of the backing layer 4046 coalesce to become salt crystals 4054 rather than dissociated species.

Figure 4E:
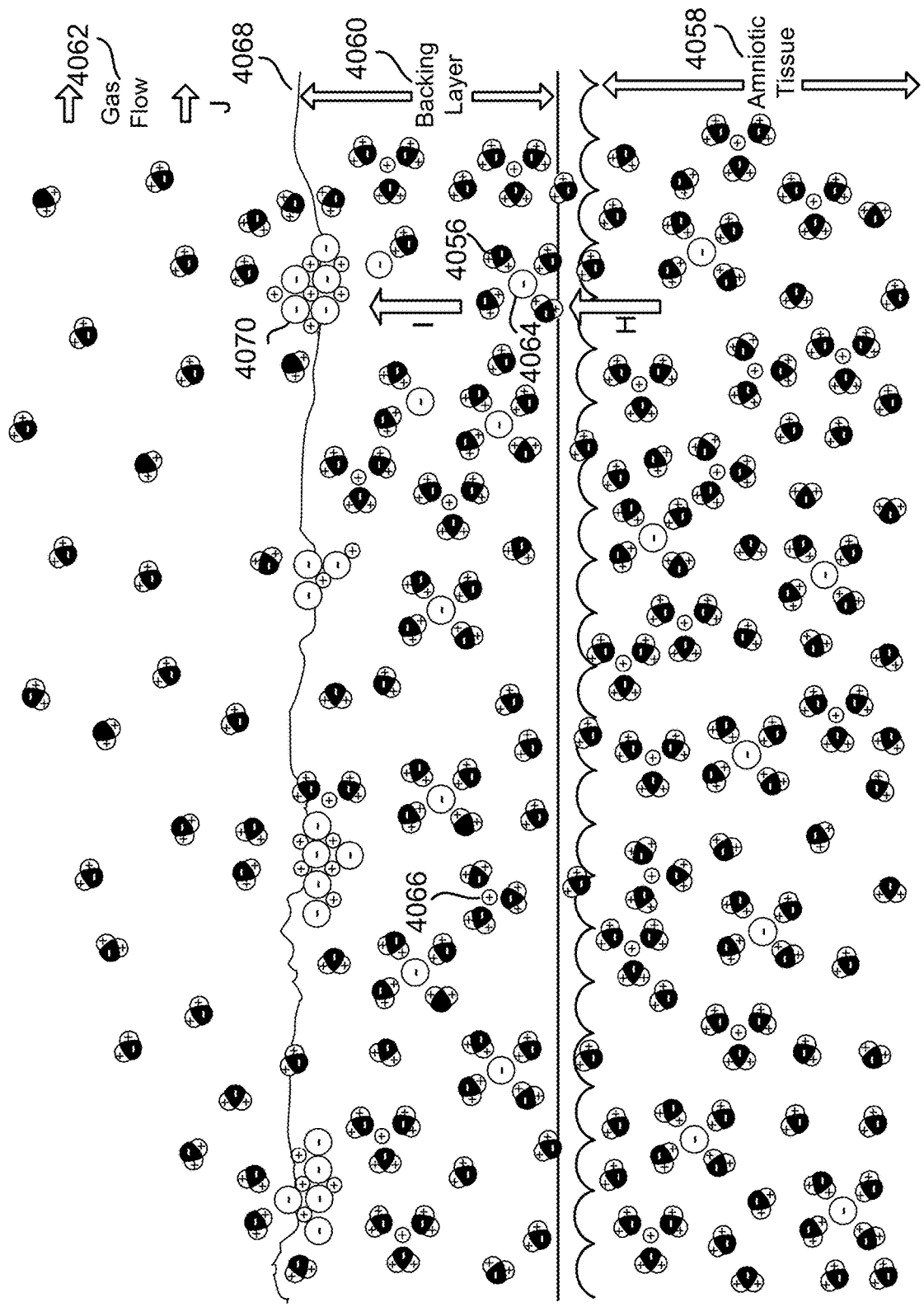

FIG. 4E shows drying at time equal to $t_4$, where $t_4$ is greater than $t_3$. Water 4056 continues to go from the amniotic tissue 4058 into the backing layer 4060. The direction of the movement of water from the amniotic tissue to the backing layer is depicted by arrows H and I. The water subsequently goes into the gas flow 4062, which moves in a direction as indicated by arrow J. Water may bring ions (anion 4064 and cation 4066) out of the amniotic tissue 4058 into the backing layer 4060. As the surface 4068 of the backing layer 4060 dries, the ions coalesce into salts 4070 at the surface 4068 of the backing layer 4060.

Figure 4F:
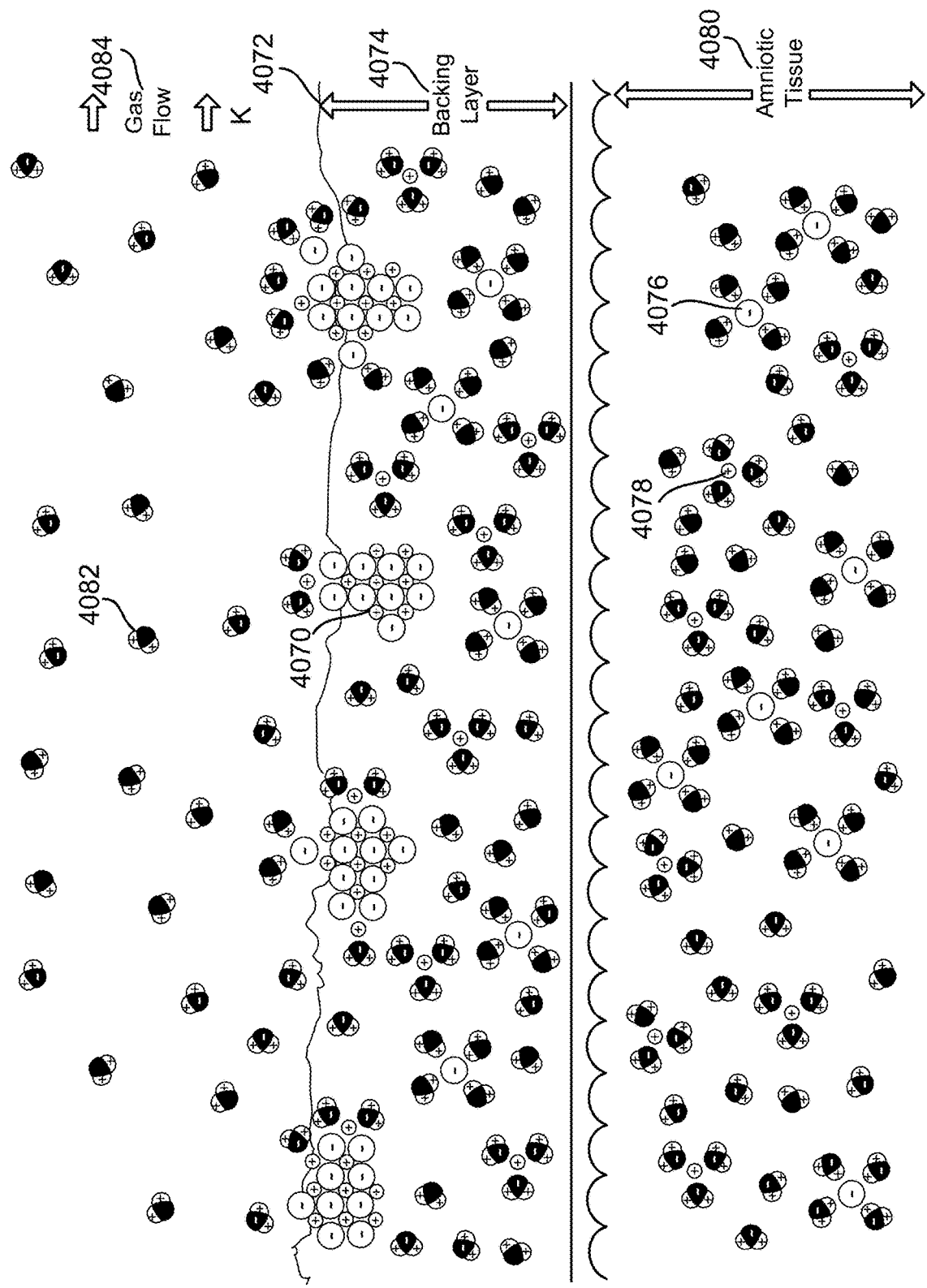

FIG. 4F shows the continuation of this process at time $t_5$, where $t_5$ is greater than $t_4$. The salt concentrations 4070 build up at the surface 4072 of the backing layer 4074, while fewer ions (anion 4076 and cation 4078) are left in the amniotic tissue 4080. Water molecules 4082 are carried away by the gas flow 4084, which moves in the direction indicated by arrow K.

Figure 4G:
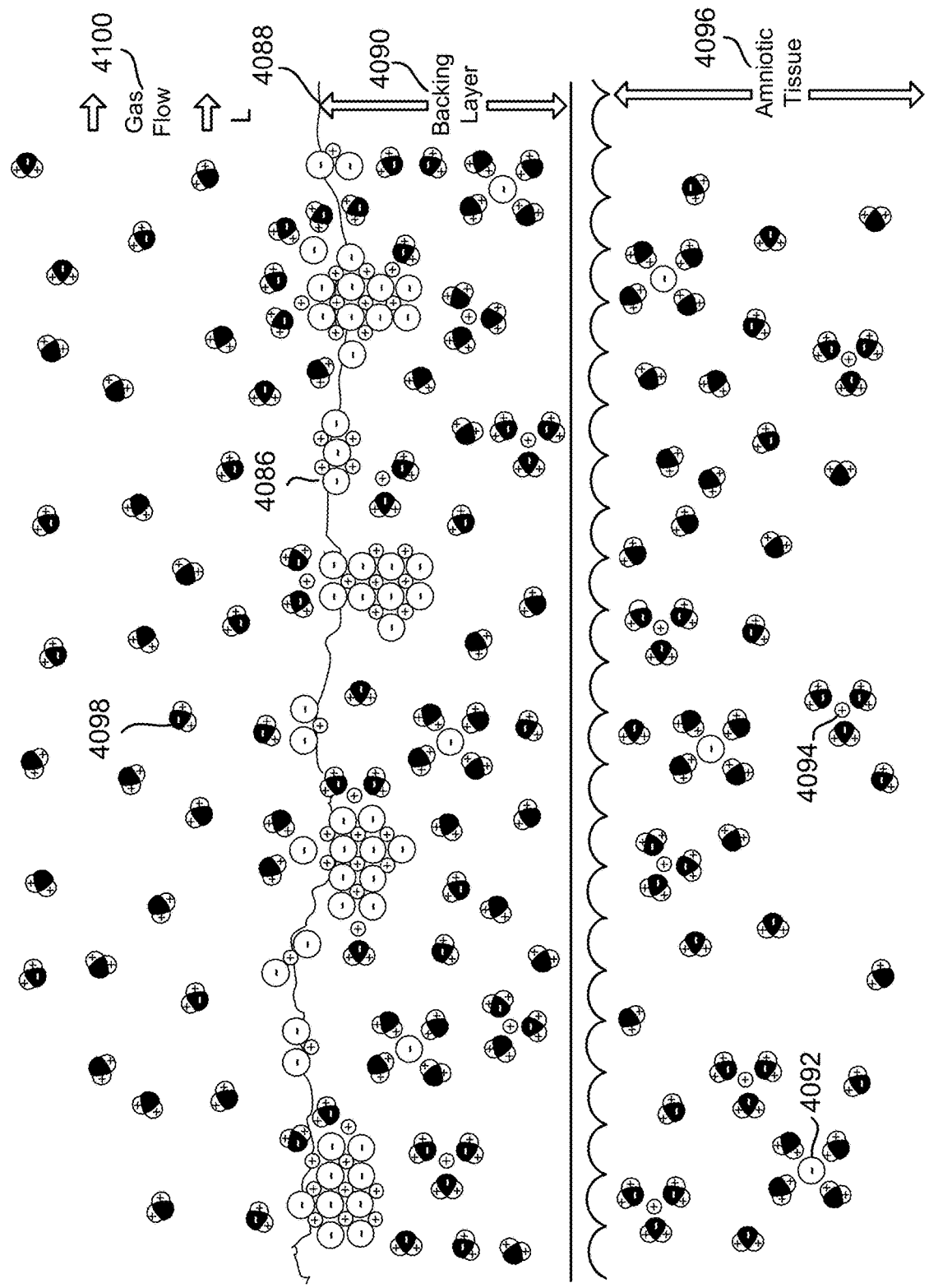

FIG. 4G shows the process at time $t_6$, where $t_6$ is greater than $t_5$. Salt crystals 4086 continue to build up at the surface 4088 of the backing layer 4090. Fewer ions (anion 4092 and cation 4094) are left in the amniotic tissue 4096. Water molecules 4098 are carried away by the gas flow 4100, which moves in the direction indicated by arrow L.

Figure 4H:
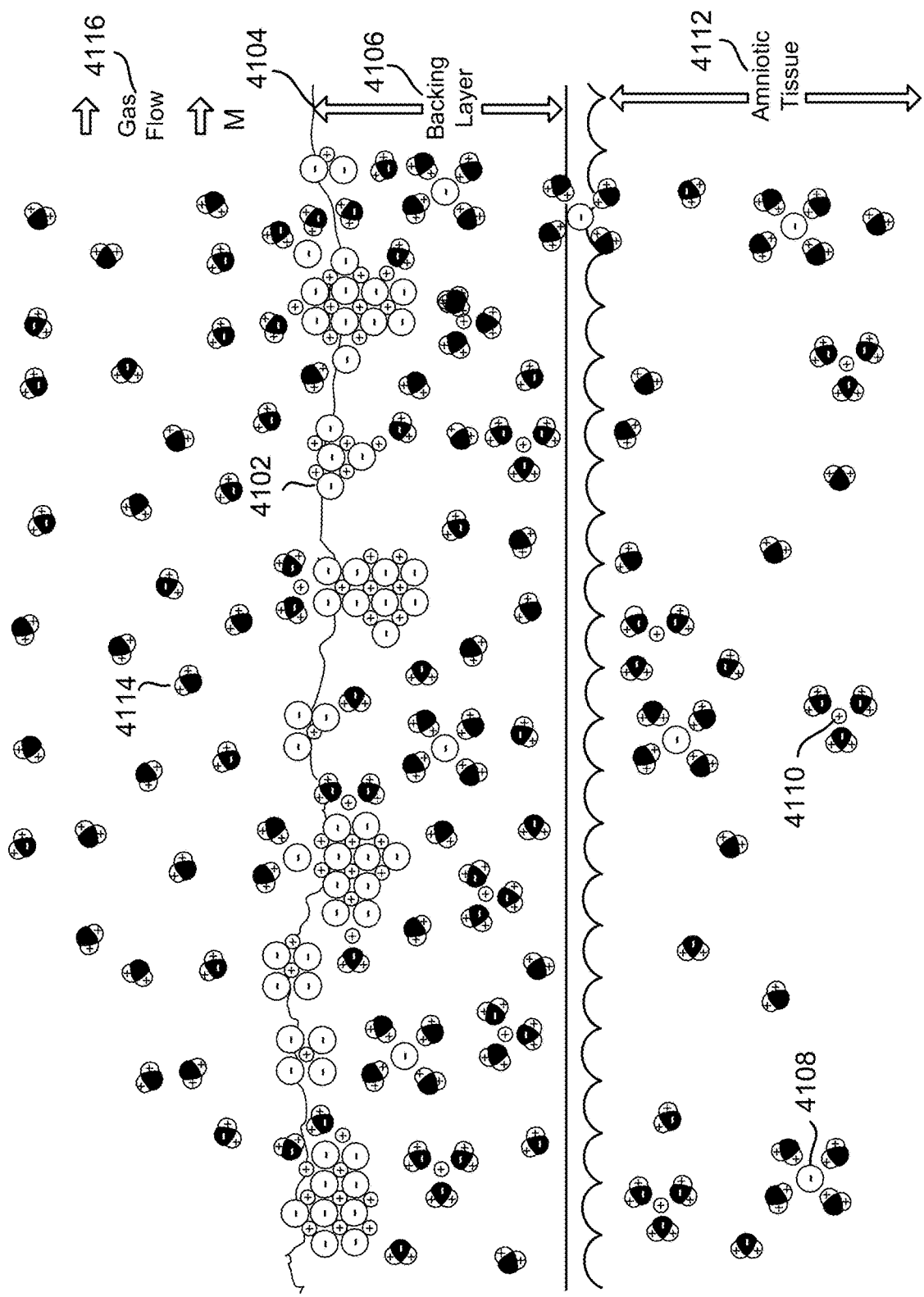

FIG. 4H shows the process at time $t_7$, where $t_7$ is greater than $t_6$. Salt crystals 4102 continue to build up at the surface 4104 of the backing layer 4106. Fewer ions (anion 4108 and cation 4110) are left in the amniotic tissue 4112. Water molecules 4114 are carried away by the gas flow 4116, which moves in the direction indicated by arrow M.

Figure 4I:
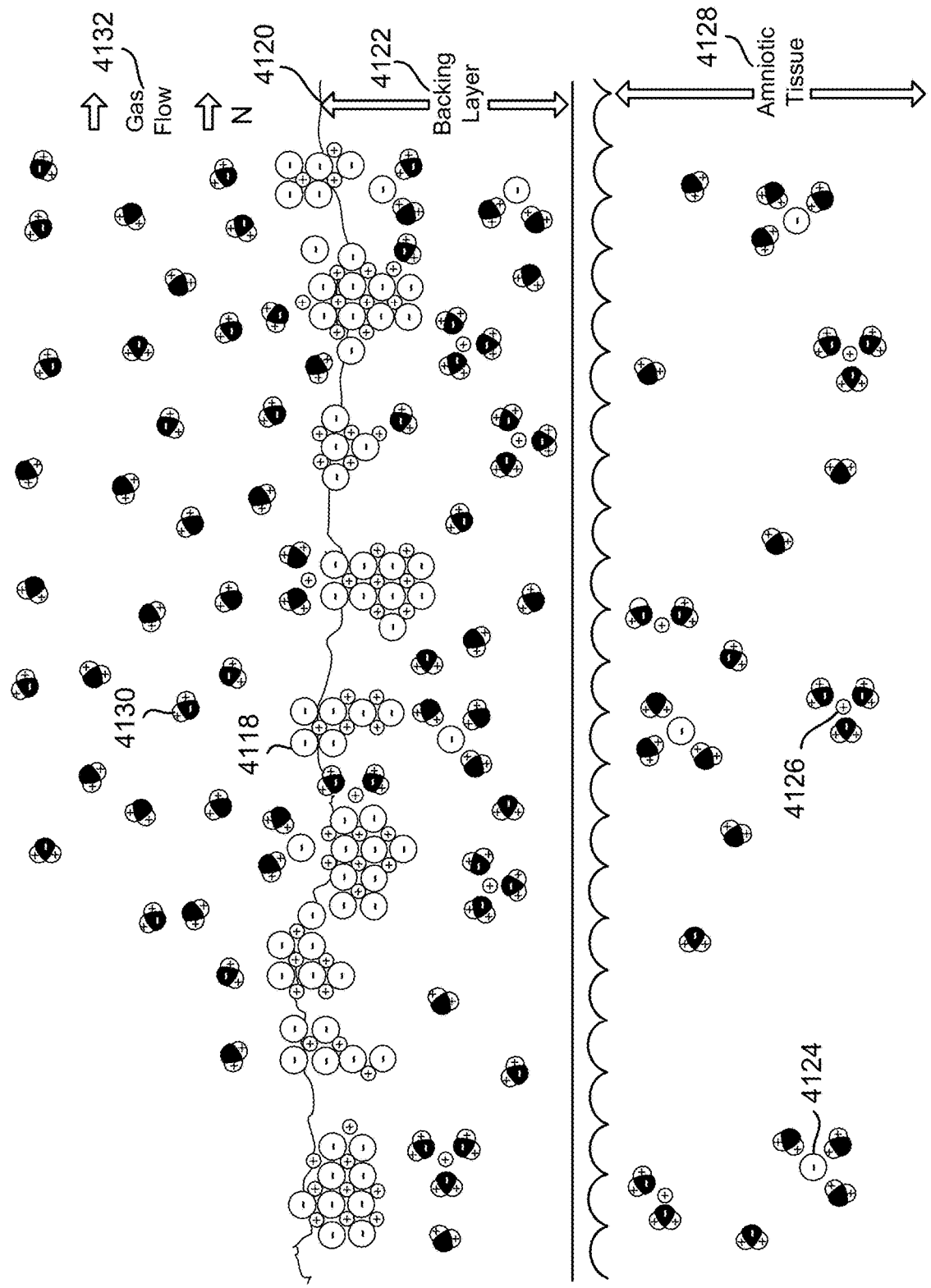

FIG. 4I shows the process at time $t_8$, where $t_8$ is greater than $t_7$. Salt crystals 4118 continue to build up at the surface 4120 of the backing layer 4122. A few ions (anion 4124 and cation 4126) remain in the amniotic tissue 4128. Water molecules 4130 are carried away by the gas flow 4132, which moves in the direction indicated by arrow N.

Figure 4J:
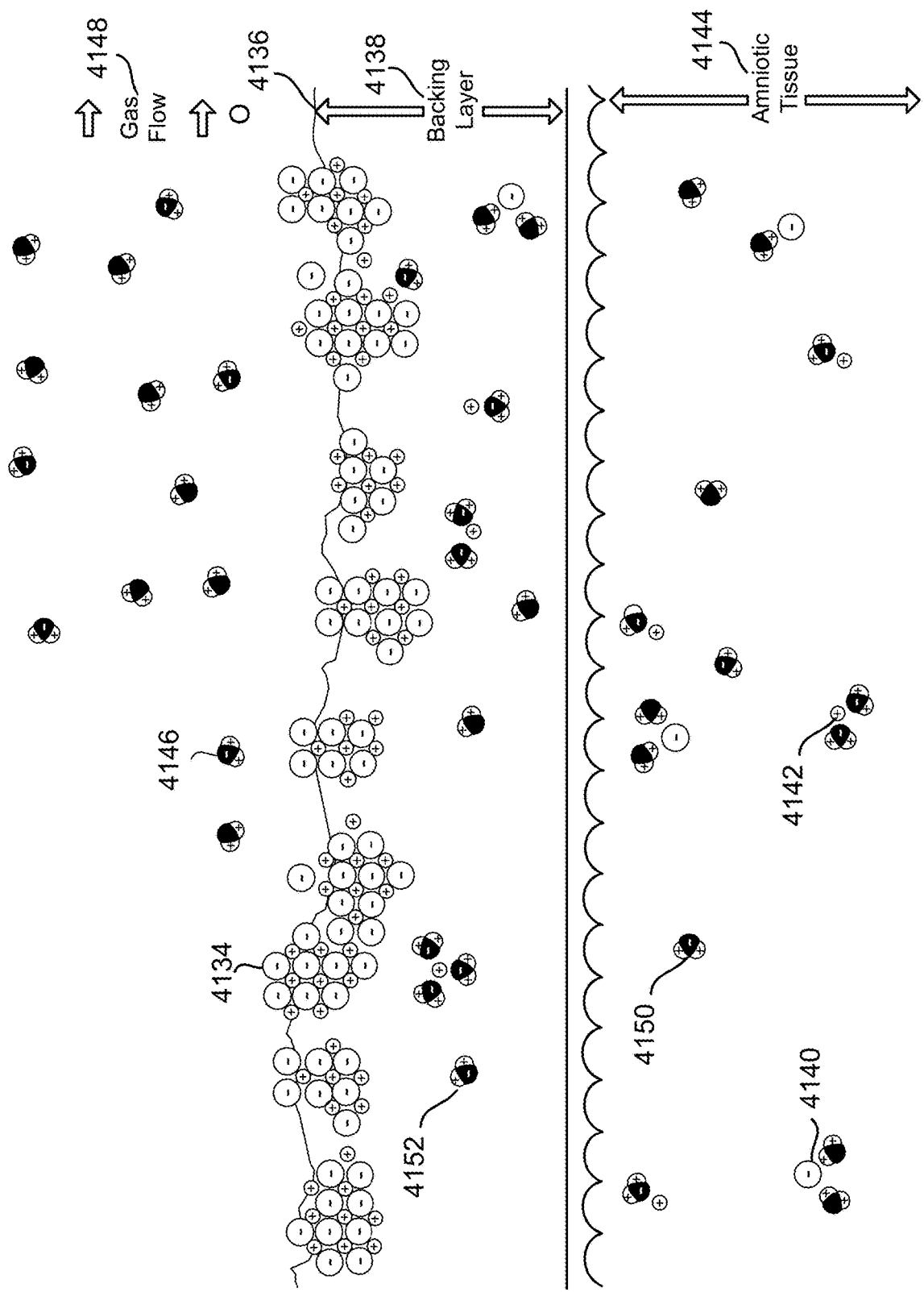

FIG. 4J shows the process at time $t_9$, where $t_9$ is greater than $t_8$. Salt crystals 4134 continue to build up at the surface 4136 of the backing layer 4138. A few ions 4140 and 4142 remain in the amniotic tissue 4144. Water molecules 4146 are carried away by the gas flow 4148, which moves in the direction indicated by arrow O. Few water molecules 4150 remain in the amniotic tissue 4144, and few water molecules 4152 are left in the backing layer 4138.

Figure 4K:
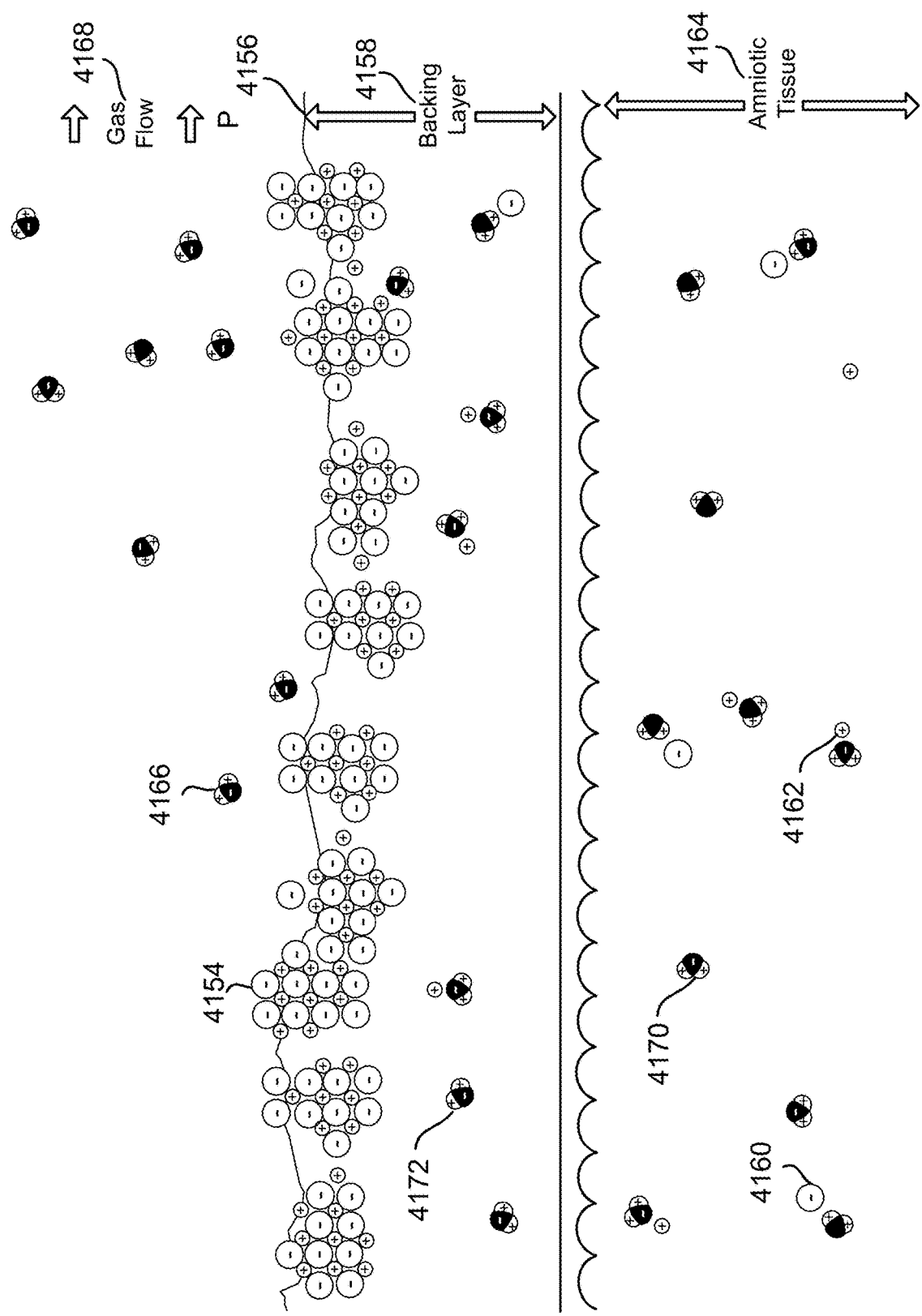

FIG. 4K shows the process at time $t_{10}$, where $t_{10}$ is greater than $t_9$. Salt crystals 4154 have almost finished building up at the surface 4156 of the backing layer 4158. A few ions (anion 4160 and cation 4162) remain in the amniotic tissue 4164. Some water molecules 4166 are carried away by the gas flow 4168, which moves in the direction indicated by arrow P. Few water molecules 4170 remain in the amniotic tissue 4164, and few water molecules 4172 are left in the backing layer 4158.

Figure 4L:
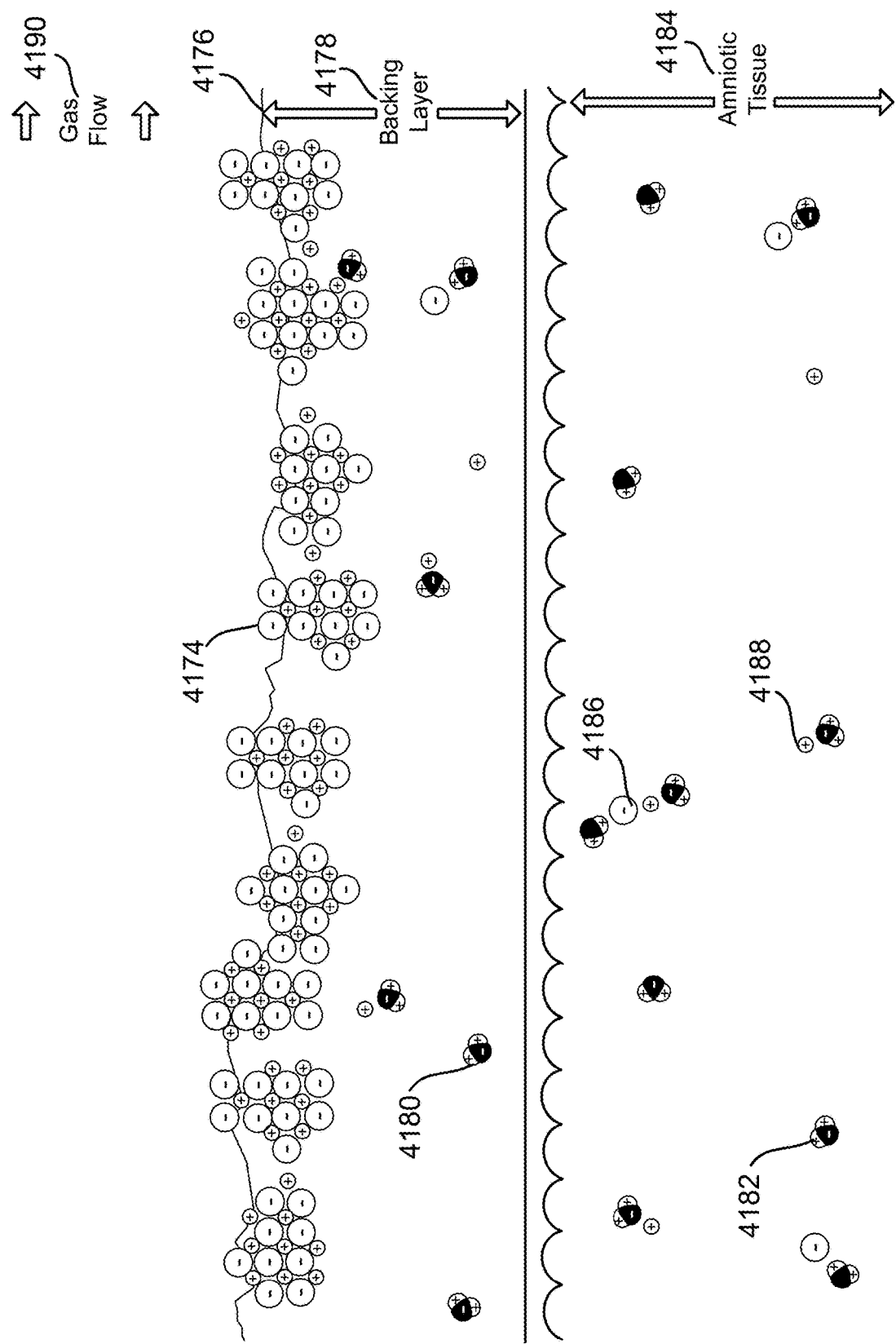

FIG. 4L shows the result at near the end of the drying process at time $t_{11}$, where $t_{11}$ is greater than $t_{10}$. Almost all of the ions coalesce as salt crystals 4174 at the surface 4176 of the backing layer 4178, while little water 4180 remains in the backing layer 4178 and little water 4182 remains in the amniotic tissue 4184. The amniotic tissue 4184 may have some ionic species (anion 4186 and cation 4188) in it but far fewer than when the process started at time $t_0$ in FIG. 4A. Although there may still be gas flow 4190, little or no water moves from the backing layer 4178 to the gas flow 4190. The drying process depicted in FIGS. 4A-4L may be carried out in a drying chamber.

Figure 5A:
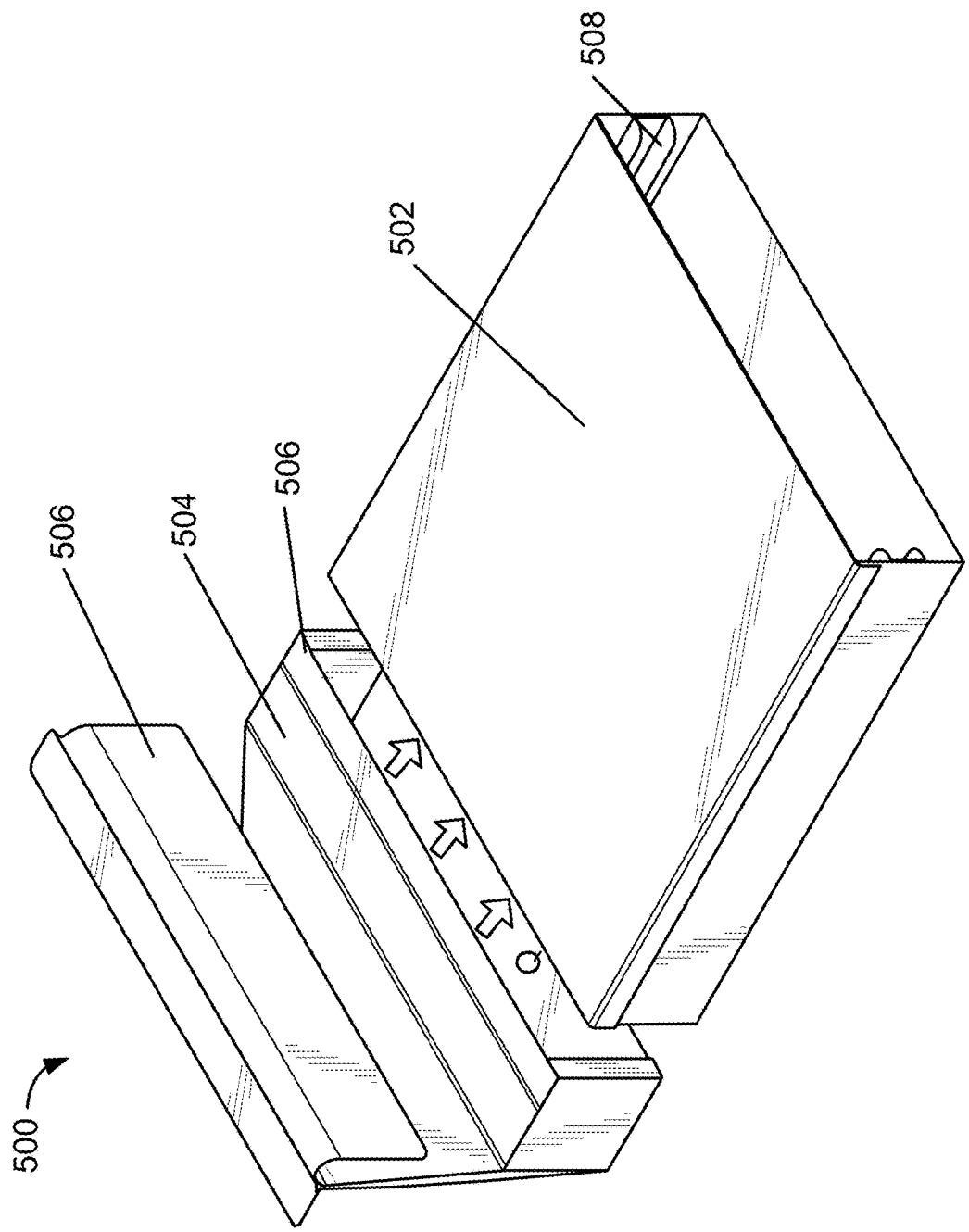
FIGS. 5A and 5B illustrate chamber assemblies used for drying the tissue, according to embodiments of the present invention.

FIG. 5A shows an embodiment of the chamber apparatus 500. The chamber box 502 has a rack 508 to receive the pressed tissue assembly sandwich 300 of FIG. 3. This chamber box 502 is attached to a shell 504 and gate 506, from which the gas flow comes, as indicated by arrows Q. The gate 506 can be closed in order to disperse the gas flow. The chamber may also operate without gate 506.

Figure 5B:
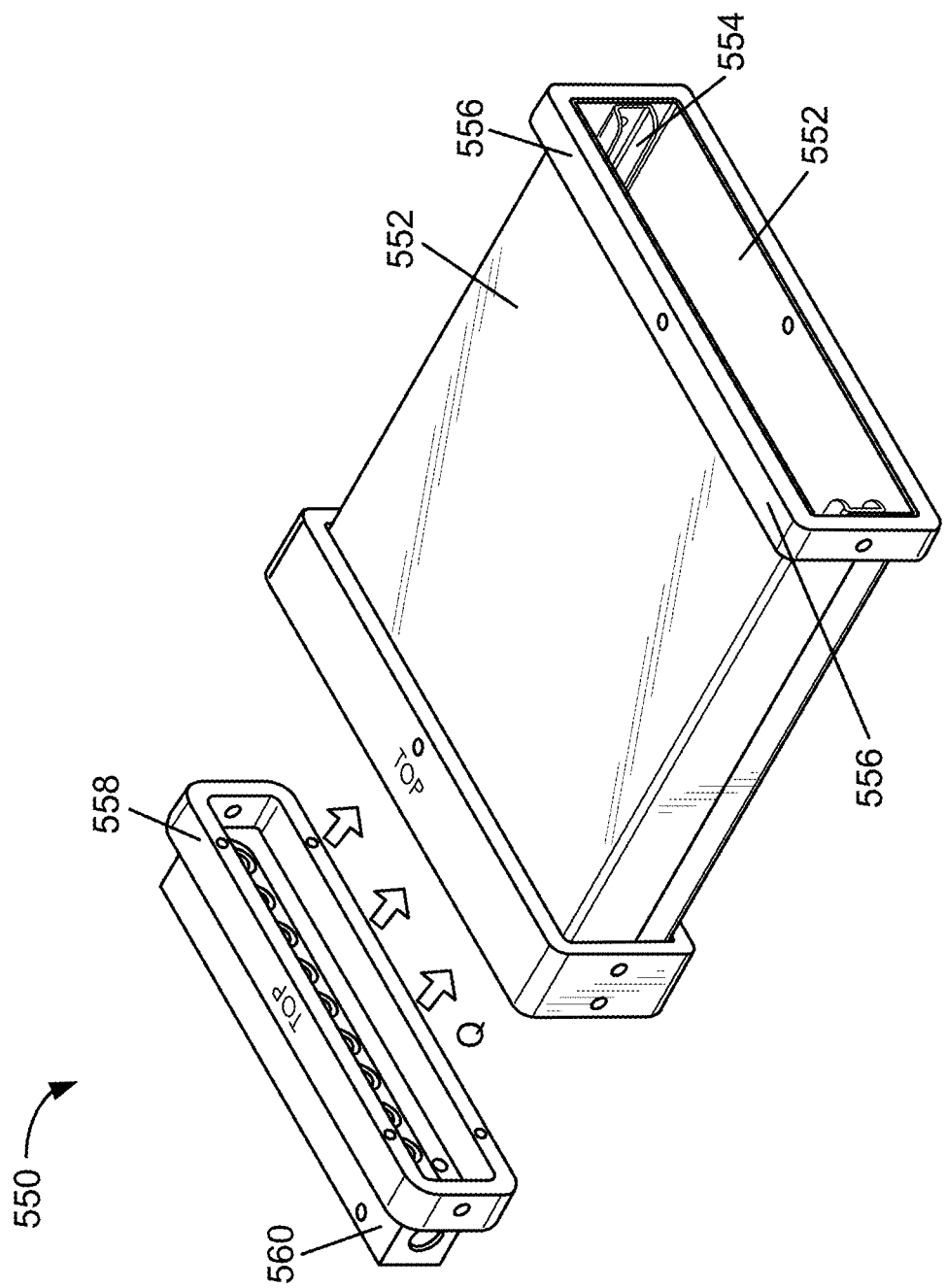

FIG. 5B shows an embodiment of the chamber apparatus 550 without a gate. The chamber box 552 has a rack 554 to receive the pressed tissue assembly sandwich 300 of FIG. 3. The chamber box 552 has a frame 556. The chamber box 552 is attached to a frame 558 coupled with a manifold 560. The manifold 560 may have a single input for gas flow and have multiple outputs. The gas flow may be represented by arrows Q. The manifold may have multiple inputs but have a greater number of outputs to distribute the gas flow substantially evenly across the width of chamber box 552. The manifold may include different spray nozzles to disperse the gas.

Figure 6A:
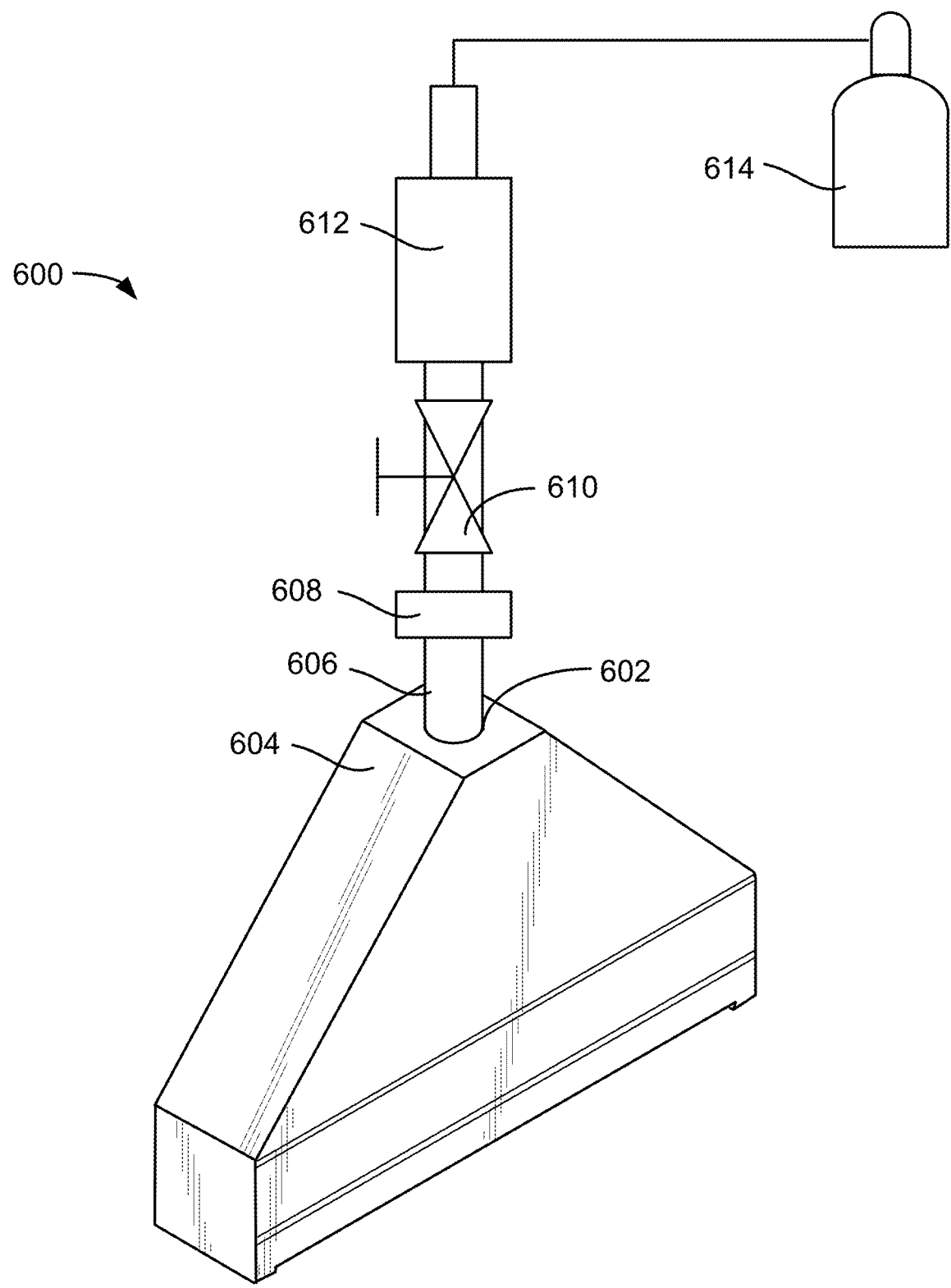
FIGS. 6A and 6B show the shell portion of the chamber assembly, according to embodiments of the present invention.

FIG. 6A shows an embodiment of the shell 600. The shell 600 is depicted as 504 in FIG. 5A. In this figure, the shell 600 may be trapezoidal in shape, with an inlet orifice 602 for the gas flow at the smaller end of the trapezoid 604. A pipe 606 delivers gas to the inlet orifice 602. The gas used to dry the tissue may be substantially free of particulates. The gas may flow through a filter 608, which may be a HEPA filter, a 0.2 μm filter, a Walker filter, a Balston/Parker filter, or another type of filter. A valve 610 can shut off the flow of gas. The pipe may be fitted with a control device 612, which can control the temperature, flow rate, quality (e.g. absence of oil, water, and/or dirt), or other characteristics of the gas flow. Although not pictured in FIG. 6A, the pipe may also include a heater (e.g., a Walker heater) and a regulator. The gas comes from a source 614, which may be a gas cylinder or an on-site supply of air. The source 614 of gas may be purified air, compressed air, nitrogen, or inert gases.

Figure 6B:
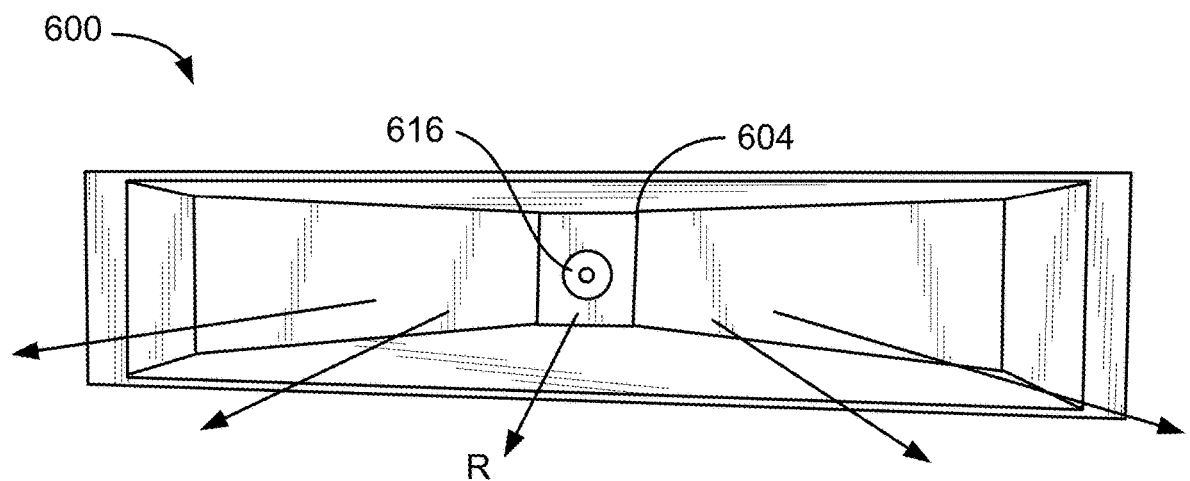

FIG. 6B shows another perspective of shell 600. A nozzle 616 may extend past the smaller end of the trapezoid 604. Upon exiting the nozzle, the gas expands, as illustrated by arrows R, through the chamber 302 of FIG. 3 to cover the width of the plate assembly.

Figure 7:
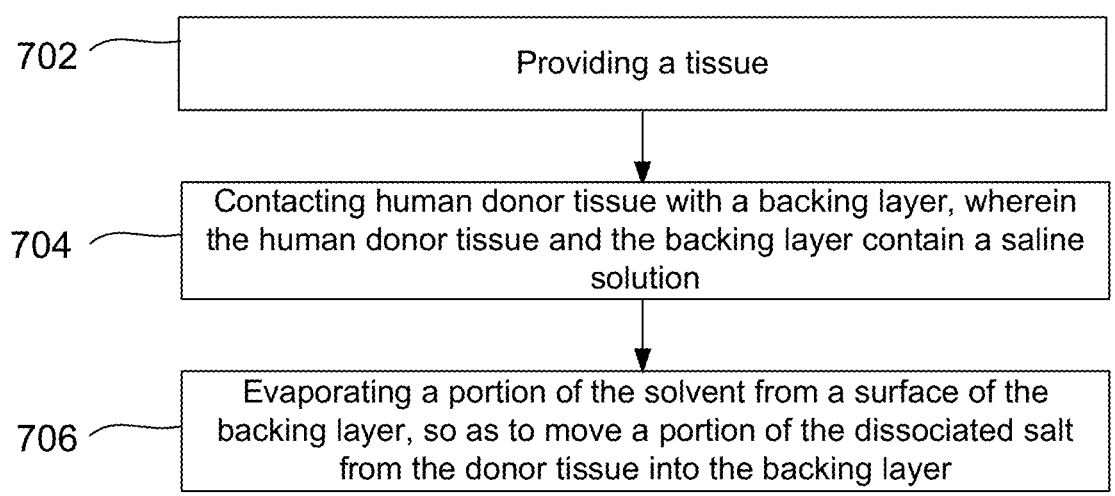
FIG. 7 shows the steps in the drying process, according to embodiments of the present invention.

FIG. 7 shows the steps involved in a drying process, according to an embodiment of the present invention. A tissue is first provided in step 702. Then in step 704, the tissue is contacted with a backing layer. Both the tissue and backing layer contain a saline solution comprising a solvent and a dissociated salt. In step 706, some of the solvent is evaporated from the surface of the backing layer. This evaporation helps move some dissociated salt from the donor tissue into the backing layer. Exemplary aspects of such drying techniques are depicted in FIGS. 4A-4L.

Figure 8:
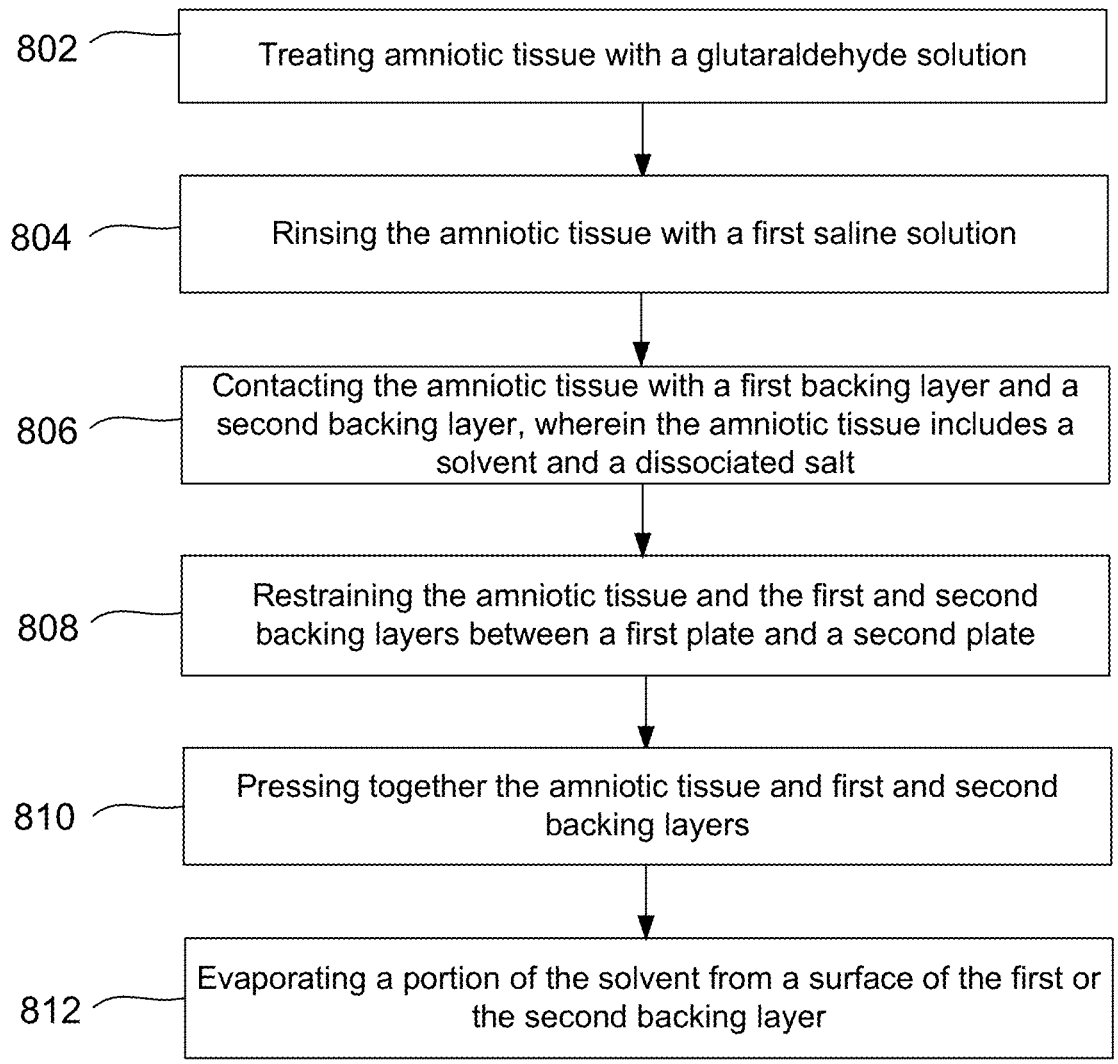
FIG. 8 shows the steps in the drying process, according to embodiments of the present invention.

FIG. 8 shows operations in a drying process according to embodiments of the present invention. Amniotic tissue is treated with a glutaraldehyde solution in step 802. In step 804, the amniotic tissue is rinsed with a first saline solution. Then in step 806, the amniotic tissue is contacted with a first backing layer and a second backing layer. The amniotic tissue may contain a second saline solution that includes a solvent and a dissociated salt. The amniotic tissue, the first backing layer, and the second backing layer may be restrained between a first plate and a second plate, as in step 808. In step 810, the amniotic tissue and the first and second backing layers may be pressed together. Then in step 812, a portion of the solvent may be evaporated from a surface of the first or the second backing layer. A portion of the dissociated salt from the amniotic tissue may move from the amniotic tissue into the first or second backing layer. Evaporating may include maintaining a temperature around the amniotic tissue below about 40° C. or may include any of the evaporating techniques described herein.

Figure 9:
FIG. 9 is a photograph of air dried amniotic tissue, according to embodiments of the present invention.

FIG. 9 is a photograph of amniotic tissue air dried with a backing layer, according to embodiments disclosed herein. This tissue has minimal wrinkles and discoloration.

Figure 10:
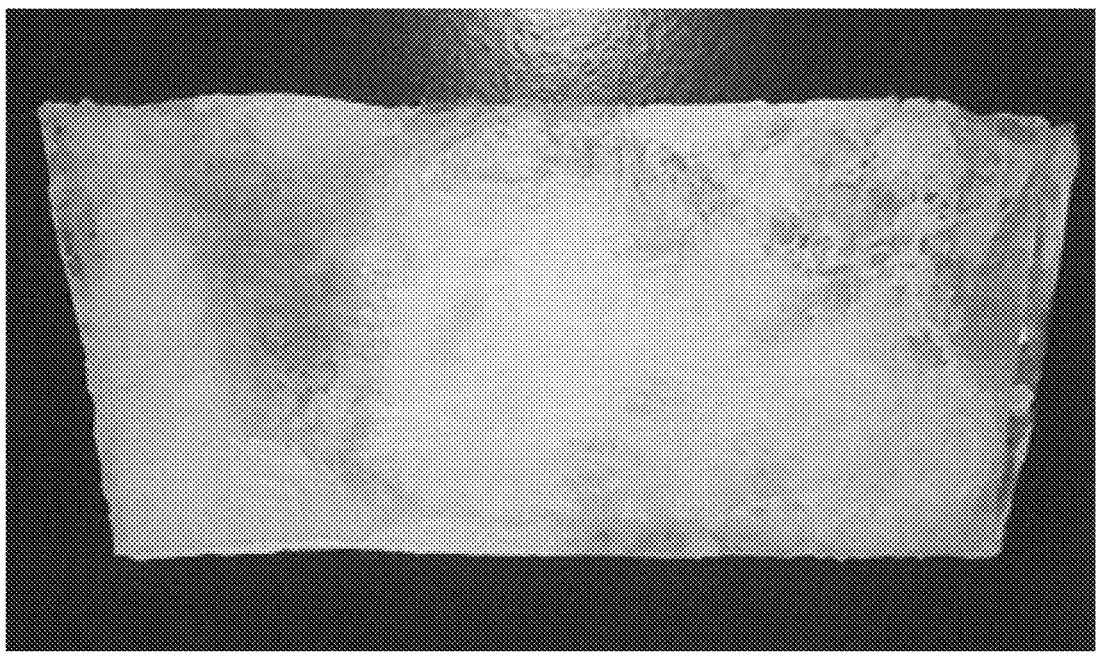
FIG. 10 is a photograph of freeze dried (lyophilized) amniotic tissue, according to embodiments of the present invention.

In contrast, FIG. 10 is a photograph of freeze dried (lyophilized) amniotic tissue. This tissue has discoloration, likely caused by salt crystals.

Figure 11:
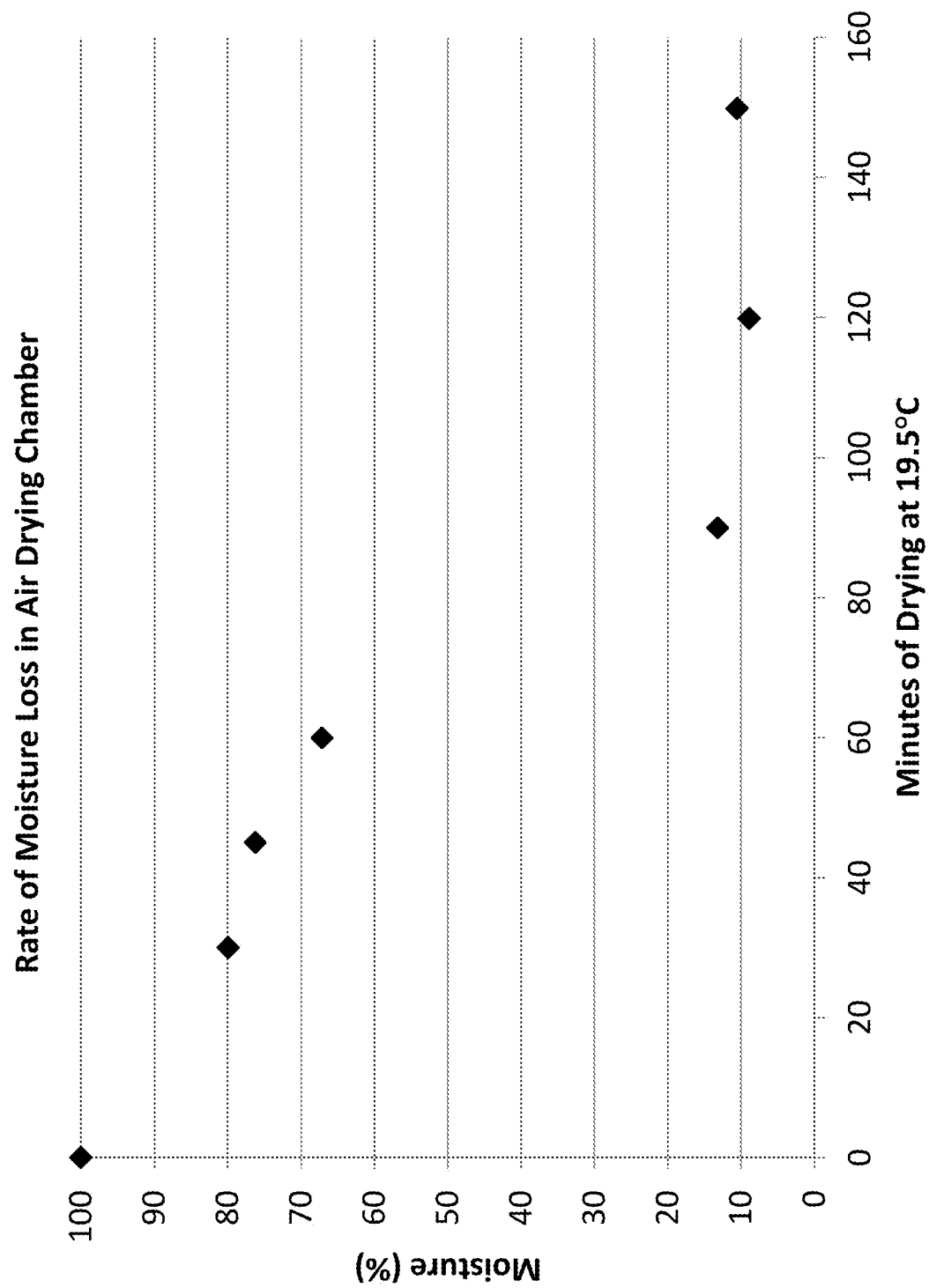
FIG. 11 is a graph of the rate of moisture loss in an air drying chamber, according to embodiments of the present invention.

FIG. 11 is a graph of the rate of moisture loss in amniotic tissue processed in an air drying chamber, according to embodiments of the present invention. After 90 min. of ambient forced air drying, the tissues reach a moisture content of less than 15%. Continued drying after the initial 90 min. does not reduce the moisture content as quickly as before the initial 90 min. The tissue has reached an equilibrium moisture level and does not easily re-adsorb moisture from the air.

Figure 12:
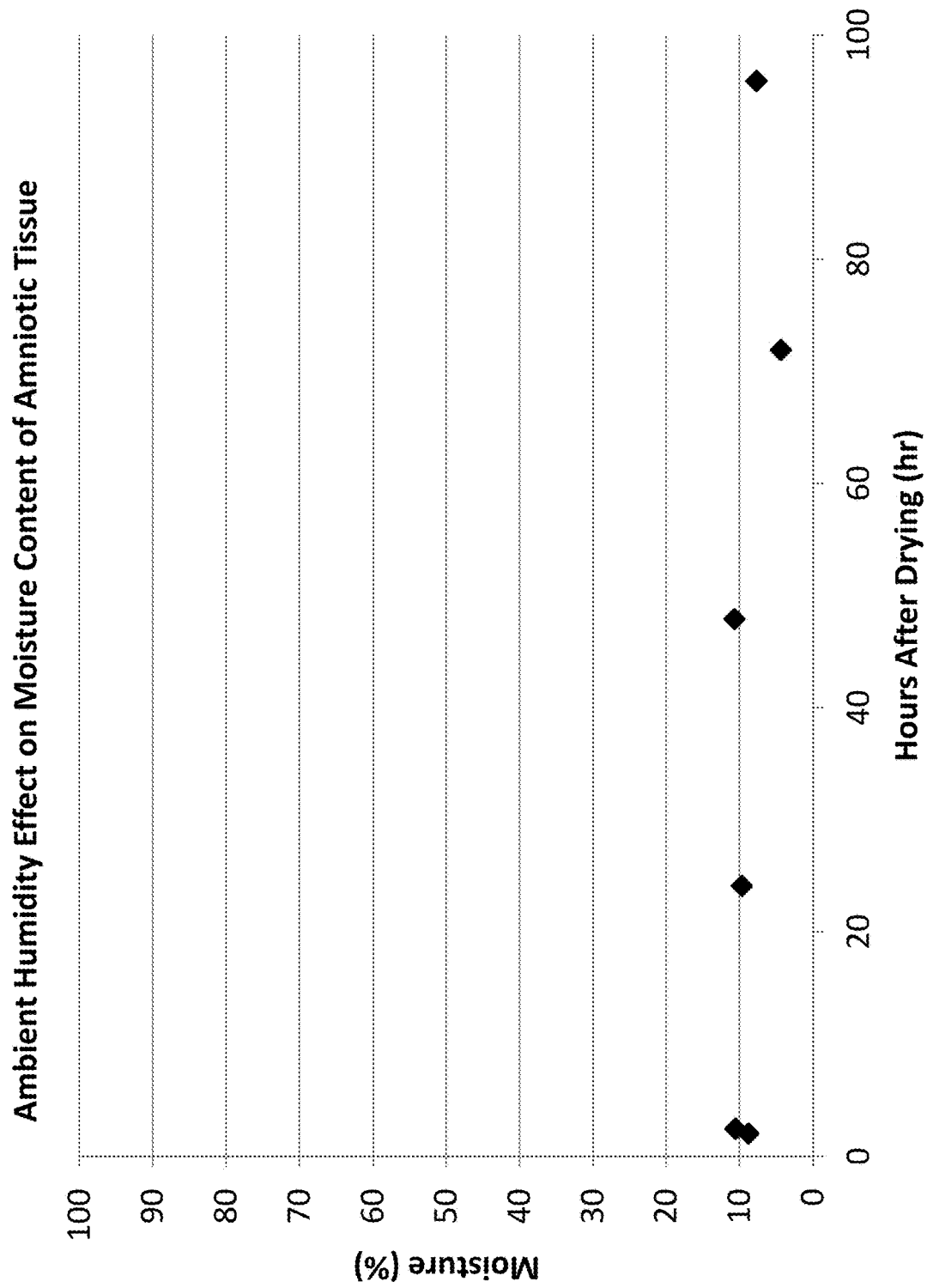
FIG. 12 is a graph of the effect of ambient humidity on the moisture content of a dried amniotic tissue, according to embodiments of the present invention.

FIG. 12 is a graph of the effect of ambient humidity on the moisture content of dried amniotic tissue, according to embodiments of the present invention. When exposed to ambient atmosphere, the tissues do not absorb a significant quantity of moisture, demonstrating that the tissue has reached an equilibrium moisture level.

Embodiments of this technology include a process of producing a dry tissue, one that is mostly free of salt crystals. The tissue may first be treated in a saline solution. The saline solution may include a salt and a solvent, which may be water. The solvent may be any solvent that evaporates gradually and any solvent in which a salt ionizes. The salt may be any salt that is ionized in the solvent. The tissue may include multiple types of salts. For example, a salt may be an inorganic salt, sodium chloride, or any salt found in amnion. The tissue may then be placed in contact with at least one backing layer to form a tissue assembly. The backing layer may also have been treated with a saline solution. Some of the solvent may be evaporated from the surface of the backing layer, whether by forced gas, heating, or other methods. When the solvent is evaporated, the solvent helps move the portion of the dissociated salt from the donor tissue to the backing layer.

The tissue may be amniotic tissue, skin tissue, fascia tissue, muscle tissue, tendon tissue, cartilage tissue, adipose tissue, or another type of human tissue. The tissue may be treated first with a glutaraldehyde solution and then rinsed with a saline solution. The tissue may also be prepared in accordance with the procedure as described in U.S. Patent Publication No. 2012/0083900 A1, whose contents are incorporated herein by reference for all purposes. With returning reference to FIG. 1, the amnion A is separated from the chorion C, and the fibroblast layer AF is intact after preparation of the amnion. The tissue may exclude chorion. The solvent in the saline solution may be water or another solvent. The tissue may have multiple layers of tissues.

The backing layer may be woven or nonwoven material. Woven or nonwoven material may be paper products, such as filters, absorbent paper, tissue paper, gauze, and wicking material. Backing layer material may be any material that can adsorb moisture and allow for passage of the migrating moisture and ions. For the nonwoven material, numerous materials could be used. Exemplary materials are ones that when the material becomes wet with solution, the moisture can be removed by the flow of gas. The moisture removed may be the solvent and may include any other liquids that may have been present in the tissue. The materials may be sterilized. The materials may also be materials that do not interact with the tissue. The backing layer may be in the form of sheets. The tissue assembly may be pressed together to assure greater surface contact between different layers of materials. This pressing may also help eliminate any air or gas pockets and may remove excess moisture.

The backing layer may be in contact with a plate. The human donor tissue and any backing layers may be restrained by at least one plate or at least two plates. With returning reference to FIG. 2, the plates 202 may be connected by a hinge 206 so that the plates 202 can close flush against each other. The plates may be perforated. A plate may be perforated so 5% to 95% of its surface area is open. In one embodiment, the plate is perforated aluminum with 79% open in the form of hexagonal holes. The plates may also be stainless steel or some other material. These plates may then be clamped around the tissue assembly. This may result in the layers shown in FIG. 3. Several different patches of tissue may fit inside one set of plates.

The evaporating or drying of the solvent could be done using the forced flow of gas around the tissue. The forced gas helps to evaporate the solvent from the saline solution in the backing layer. With returning reference to FIG. 4B and without being bound to any particular theory, water may first move from the backing layer to the gas flow. This may create a lower concentration of moisture in the backing layer and a concentration gradient from the amniotic tissue to the backing layer. As shown in FIGS. 4C-4K, water then migrates from the higher concentration in the tissue to the lower concentration in the backing layer. As shown in FIGS. 4C-4L, the movement of water also may help drive salt ions from the tissue into the backing layer. The ions may eventually gather near the surface of the backing layer, forming salt crystals 4054, as shown in FIG. 4D. FIGS. 4E-4L show these crystals growing larger. At the end of drying, the tissue may be largely free of moisture and salt crystals. The backing layer may be largely free of moisture but have salt crystals 4174 on its surface, as depicted in FIG. 4L. This drying process may then leave behind a pliable tissue with only trace amounts of salt and a moisture content of about 10%. The plates and the tissue assembly may allow the tissue to dry flat and without wrinkling as it dries. The tissue may then be a flat smooth sheet that is flexible and dry to the touch. This tissue then may be easier to handle and manipulate prior to implantation.

The drying in the chamber may be done with gas flow but without the addition of heat. Heated may be added directly to the chamber or the gas flow may be heated prior to the gas entering the chamber. Gas flow rates may be from 3 gallons per minute to 10 gallons per minute. The drying may also be done in temperatures from about 5° C. to about 40° C. Drying in gas flow may be done for at least 1.5 hours and may be less than 3 hours. In addition, drying may be performed by moving the plates and the tissue assembly mechanically. This movement may be in a radial direction like a windmill or fan, in a linear direction, or in a direction that may be both radial and linear. Mechanical movement may reduce the amount of gas flow needed for drying.

The drying process may be performed without a desiccant.

The final moisture content of the tissue may be less than 10%, including less than 5%. The amount of moisture left in the tissue may reach an equilibrium point. At the equilibrium moisture, when the tissue is left in ambient air for a long time, including times of several days, the tissue will not gain a significant amount of moisture from the ambient air.

The final concentration of salt left may be from about 0.03% to about 0.18% by weight of the weight of the final product tissue. For example, the final concentration of the salt may be from about 0.03% to about 0.10%, from about 0.03% to about 0.15%, from about 0.04% to about 0.09%, or about 0.07% by weight of the weight of the final product tissue. The tissue may not be completely salt free.

After the drying is done, the backing layer may be removed from the tissue. Any areas of discoloration or other non-uniformities may be trimmed from the tissue. The tissue also may later be rehydrated with a liquid comprising water or saline solution (e.g., 0.9% saline solution). The saline solution may have a concentration of less than about 0.9%. Rehydradtion may involve soaking by flow of solvent, immersion in a solvent, or soaking the implant with a solvent by irrigation. In some cases, the wetting solvent may be fluids from the surgical site of the implant.

Salt content may have an effect on the rate of rehydration. A tissue with a higher salt content may rehydrate more quickly than a tissue with lower salt content. If a tissue rehydrates too quickly, the tissue may cling to itself. The tissue may ball up and no longer resemble a flat sheet, making the tissue difficult to apply to a patient. A medical practitioner may want to reposition the tissue after its initial application and too fast of a rehydration rate may make repositioning the tissue difficult. Embodiments of the present technology include tissues that rehydrate over minutes rather than seconds. When water is applied to these tissues, the water may initially bead up on the tissue.

In another aspect, an embodiment of this technology may be an apparatus for drying human donor tissue. This tissue drying apparatus may include the tissue placed in contact with at least one backing layer. This tissue assembly may be restrained by two plates, similar to those shown in FIG. 2. The tissue may be amniotic tissue or other tissue derived from humans. The tissue may also come from animals.

The tissue may be placed in contact with a second backing layer. The backing layer may be made of woven or nonwoven material. The material may also be wetted with saline solution. For amniotic tissue, the backing layer may be placed on the epithelial surface of the amniotic tissue. At least one of the plates may be perforated.

The tissue drying apparatus may also include the chamber, as shown in FIG. 5, that can receive the plates, tissue, and backing layer. The chamber may also be configured to receive more than one set of plates. This chamber may have an inlet to allow for gas to flow through the chamber and around the plates in order to dry the tissue and backing layer. The gas may be delivered to the chamber through the use of a pipe, tube, manifold, or other device. A filter may be included as part of the gas delivery system in order to remove unwanted contaminants. The gas may also be delivered into the chamber by a nozzle 616 in FIG. 6B. This nozzle may extend some distance into the chamber rather than be flush with the chamber wall, in order to deliver better quality gas flow to the tissues and plates. The chamber may be configured with other gas dispersion techniques.

The tissue dried by this process may be mostly salt crystal free, pliable, with minimal wrinkles. The tissue may appear as shown in FIG. 7. The tissue may have a consistent appearance, including areas that appear white or chalky. In contrast, a tissue dried by freeze drying may have the discoloration shown in FIG. 10. The tissue dried by freeze drying may be dominated by white discoloration, which may appear in blotches.

EXAMPLES

Example 1

Tissue from amniotic donors is processed by removing the amnion from the placenta by blunt dissection and then clearing the chorion, Wharton's jelly, and blood from the amnion by rinsing and scraping with gloved finger tips. The tissue is treated with 1% glutaraldehyde for 15 minutes and then rinsed with three 400 mL volumes of 0.9% saline solution. Once the tissue is rinsed, the amnion is spread on a cutting surface, stromal side down, and precut pieces of backing material are placed on the epithelial surface. In this example, the backing layer is a DELNET apertured films product (DELNET 3.3 NPET-E non-woven backing material, available from DelStar Technologies, Inc.) and has a sticky side and a non-sticky side. In this case, the sticky side viewed under a microscope resembles the loop part of a VELCRO fastener, and the non-sticky side is similar to the white pad of an adhesive bandage. Here, the non-sticky side of the backing layer is placed in contact with the epithelial side of the amnion. The amnion is cut with a scalpel to the shape of the backing layer, and the backing with the amnion is flipped over. The amnion is adjusted to assure that the amnion is flat and spread evenly over the backing layer. A second patch is then cut the same way, and the two patches are assembled into a sandwich of four layers: backing layer-amnion-amnion-backing layer. The two amniotic stromal surfaces are then pressed together between two plates, as shown in FIG. 3. These samples are in sizes of 2×2, 2×4, 4×4, 4×8, and 8×16 cm.

Example 2

After the tissues are pressed, the tissues and backing layers are placed between two stainless steel perforated plates and clamped together to keep the sandwiched assembly together. The stainless steel plate is then placed in a BIO-RAD GELAIR dryer. The fan is turned on with no heat, and the sandwiched assembly is allowed to dry to its equilibrium point. With no heat, the temperature ranges from between 18 and 25° C. Experimental determination of the equilibrium point is described in Example 4.

To determine the time required to dry double-sided amnion (the two amnion layers in the sandwich) in a chamber with positive ambient airflow, tissue samples are dried for varying amounts of time and the moisture content of the samples is measured. A separate set of four samples is pulled at times of 30, 45, 60, 90, 120, and 150 minutes. After the sample is exposed for a specific time, the samples are labeled and immediately placed in an individual KAPAK pouch and sealed to prevent the continued evaporation or gain of moisture. After all samples are collected, each sample is pulled from the backing layer. The sample is weighed and then placed in a 100° C. oven for 30 minutes and then re-weighed. The difference in weight is attributed to moisture loss. Results are shown in Table 1 and in FIG. 11.

TABLE 1

| Time (min.)  | 0     | 30   | 45   | 60   | 90   | 120 | 150  |
|--------------|-------|------|------|------|------|-----|------|
| Moisture (%) | 100.0 | 80.1 | 76.2 | 67.3 | 13.2 | 8.8 | 10.4 |

Example 3

The dried samples are then exposed to ambient atmosphere (temperature at 21±4° C.) and weighed at times to see if the samples gained water or remained dry. The amnion tissues do not appear to absorb significant quantities of moisture when exposed to the ambient atmosphere. Results are shown in Table 2 and FIG. 12.

TABLE 2

| Time (hr)    | 2   | 2.5  | 24  | 48   | 72  | 96  |
|--------------|-----|------|-----|------|-----|-----|
| Moisture (%) | 8.8 | 10.4 | 9.7 | 10.7 | 4.5 | 7.6 |

Example 4

In order to determine the moisture equilibrium point for amniotic tissues, 20 amniotic tissue assemblies are exposed to ambient humidity of between 14% and 17% for two hours. These tissue assembles had previously been treated with a saline solution and then dried previously during processing. Each tissue assembly is weighed then placed in a 100° C. oven and allowed to warm for 30 minutes. Immediately after the 30 minutes, each tissue assembly is weighed again and the difference in weight measurements attributed to moisture loss. In this experiment, the average loss of weight is 4.9% with a high value of 7.6% and the low value of 1.2%. This experiment included 11 4×8 cm patches and nine 4×4 centimeter patches. This experiment shows an equilibrium moisture level of under 11%.

Example 5

Other amnion drying methods have also been explored. Freeze drying at a pressure less than 10 mTorr for 12 hours caused the patch to take on a chalky white inconsistent appearance from the salt, as shown in FIG. 10. Oven drying at a temperature greater than 40° C. for 30 minutes caused the patch to turn a dark brown and appear more brittle. Air drying with no backing layer left the patch with excessive wrinkling and size deformation.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the layer" includes reference to one or more layers and equivalents thereof known to those skilled in the art, and so forth.

What is claimed is:

1. An apparatus comprising:
a human donor tissue;
a backing layer, wherein:
the human donor tissue is in contact with the backing layer, and
the backing layer comprises an absorbent material that allows for passage of moisture and ions;
a first plate;
a second plate, wherein:
the first plate and the second plate restrain the human donor tissue and the backing layer, and
the first plate and the second plate are parallel to a first direction;
a chamber;
a gas inlet, wherein:
the gas inlet is configured such that a gas flowing through the gas inlet flows in the first direction; and
a manifold defining a plurality of outputs, wherein:
the manifold is configured such that gas flowing from the gas inlet to the chamber passes through the manifold and is distributed substantially evenly by the plurality of outputs across a second direction in the chamber, and
the second direction is perpendicular to the first direction.

2. The apparatus of claim 1, wherein the chamber is configured to receive the first plate, the second plate, the human donor tissue, and the backing layer.

3. The apparatus of claim 2, wherein the chamber is configured to allow forced gas to flow around the first plate and the second plate.

4. The apparatus of claim 2, wherein the chamber is configured for heating.

5. A system for drying human donor tissue for administration to a recipient patient, the system comprising:
a first plate;
a second plate, wherein the first plate and the second plate are connected by hinges;
a chamber;
a gas inlet; and
a manifold defining a plurality of outputs;
wherein:
the chamber is configured to receive the first plate and the second plate when the first plate and the second plate are substantially parallel to each other and substantially overlap, the gas inlet is in fluid communication with the chamber, the gas inlet is configured such that a gas flowing through the gas inlet to the chamber flows in a first direction, the manifold is configured such that gas flowing from the gas inlet to the chamber passes through the manifold and is distributed substantially evenly by the plurality of outputs across a second direction in the chamber, the second direction is perpendicular to the first direction, and the chamber is configured such that when the first plate and the second plate are disposed in the chamber:

the gas flowing through the gas inlet and the plurality of outputs flows over the first plate and under the second plate, and the first plate and the second plate are parallel to the first direction.

6. The system of claim 5, further comprising a heater.

7. The system of claim 5, further comprising the human donor tissue.

8. The system of claim 7, wherein the human donor tissue is in contact with a backing layer, and the backing layer comprises an absorbent material that allows for passage of moisture and ions.

9. The system of claim 7, wherein the human donor tissue is disposed between the first plate and the second plate.

10. The system of claim 5, wherein at least one of the first plate and the second plate is perforated so that 5% to 95% of the first plate or second plate is open.

11. The system of claim 10, wherein the first plate is perforated with hexagonal holes.

12. The system of claim 5, further comprising:
a shell,
wherein:
the shell comprises the gas inlet,
the shell comprising a first end and a second end,
the first end is smaller than the second end,
the gas inlet is nearer the first end than the second end,
the shell is attached to the chamber, and
the chamber is nearer the second end than the first end.

13. The system of claim 5, further comprising a filter in fluid communication with the gas inlet.

14. The system of claim 5, wherein the system excludes a heater directly heating the chamber.

15. The system of claim 5, further comprising a gas source.

16. The system of claim 5, wherein the first plate and the second plate comprise stainless steel.

17. The system of claim 10, wherein at least one of the first plate and the second plate is perforated so that 70% to 95% of the first plate or second plate is open.

18. The system of claim 5, wherein the gas flowing through the gas inlet flows over the first plate in the first direction and under the second plate in the first direction.

* * * * *